(12) United States Patent  (10) Patent No.: US 8,290,120 B2
Bjorkholm  (45) Date of Patent: Oct. 16, 2012

(54) DUAL ENERGY RADIATION SCANNING OF CONTENTS OF AN OBJECT BASED ON CONTENTS TYPE

(75) Inventor: Paul Bjorkholm, Newport Beach, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 402 days.

(21) Appl. No.: 12/587,063

(22) Filed: Sep. 30, 2009

(65) Prior Publication Data

US 2011/0075800 A1   Mar. 31, 2011

(51) Int. Cl.
*G01N 23/06* (2006.01)
*G01N 23/04* (2006.01)

(52) U.S. Cl. ............................. 378/53; 378/57
(58) Field of Classification Search ............. 378/51, 378/53, 57, 62
See application file for complete search history.

(56) References Cited

U.S. PATENT DOCUMENTS

| | | |
|---|---|---|
| 4,540,882 A | 9/1985 | Vinegar et al. |
| 5,524,133 A | 6/1996 | Neale et al. |
| 5,682,411 A | 10/1997 | Rushbrooke et al. |
| 5,838,758 A | 11/1998 | Krug et al. |
| 5,917,880 A | 6/1999 | Bjorkholm |
| 6,069,936 A | 5/2000 | Bjorkholm |
| 6,088,423 A | 7/2000 | Krug et al. |
| 6,195,444 B1 | 2/2001 | Simanovsky et al. |
| 6,438,201 B1 | 8/2002 | Mazess et al. |
| 6,449,334 B1 | 9/2002 | Mazess et al. |
| 6,816,571 B2 | 11/2004 | Bijjani et al. |
| 6,937,692 B2 | 8/2005 | Johnson et al. |
| 6,944,264 B2 | 9/2005 | Bijjani et al. |
| 7,023,957 B2 | 4/2006 | Bijjani et al. |
| 7,103,137 B2 | 9/2006 | Seppi et al. |
| 7,130,371 B2 | 10/2006 | Elyan et al. |
| 7,158,611 B2 | 1/2007 | Heismann et al. |
| 7,257,188 B2 | 8/2007 | Bjorkholm |
| 7,397,891 B2 | 7/2008 | Johnson et al. |

(Continued)

FOREIGN PATENT DOCUMENTS

JP   6-504838   6/1994

(Continued)

OTHER PUBLICATIONS

Moore et al; "Better Imaging: The Key to Better Cargo Inspection" Port Technology International, 2001, pp. 113-119.

(Continued)

*Primary Examiner* — Irakli Kiknadze
(74) *Attorney, Agent, or Firm* — Brandon N. Sklar, Esq.; Kaye Scholer LLP

(57) ABSTRACT

Methods for selecting and applying test criterion for use in the radiation analysis of contents of objects, based on whether the contents of the object, or contents of portions of the object, comprise inorganic or organic material, are described. In one example, the object is scanned by radiation and the contents type is determined based on preliminary test criterion adapted to distinguish between inorganic material and organic material, and detected radiation. At least one test criterion is selected based, at least in part on the determination and it is then determined whether the object at least potentially contains material having an atomic number greater than a predetermined atomic number based, at least in part, on the detected radiation and the at least one selected test criterion. Systems are also disclosed.

33 Claims, 20 Drawing Sheets

U.S. PATENT DOCUMENTS

| | | |
|---|---|---|
| 7,423,273 B2 | 9/2008 | Clayton et al. |
| 7,636,417 B2 | 12/2009 | Bjorkholm |
| 7,769,132 B1 * | 8/2010 | Hurd et al. ................ 378/57 |
| 2003/0190011 A1 | 10/2003 | Beneke et al. |
| 2004/0256565 A1 | 12/2004 | Adams et al. |
| 2004/0258189 A1 | 12/2004 | Norman et al. |
| 2007/0210255 A1 | 9/2007 | Bjorkholm |
| 2008/0205594 A1 | 8/2008 | Bjorkholm |

FOREIGN PATENT DOCUMENTS

| | | |
|---|---|---|
| JP | 7-505216 | 6/1995 |
| JP | 8-68768 A | 3/1996 |
| WO | WO 92/02892 | 2/1992 |
| WO | WO 93/14419 | 7/1993 |
| WO | WO 97/18462 | 5/1997 |
| WO | WO 01/27601 A1 | 4/2001 |
| WO | WO 03/067770 A2 | 8/2003 |
| WO | WO 2005/008586 A2 | 1/2005 |

OTHER PUBLICATIONS

S. Ogorodnikov, V. Petrunin, 'Processing of interlaced images in 4-10 MeV dual energy customs system for material recognition', Physical Review Special Topics—Accelerators and Beams, 2002, vol. 5, The American Physical Society, College Park, MD.

S. Ogorodnikov et al., "Radioscopic Discrimination of Materials in 1÷10 MeV Range for Customs Applications"; 8th European Particle Accelerator Conference, Paris, France, Jun. 3-7, 2002, pp. 2807-2809; Available at http://accelconf.web.cem.ch/accelconf/e02/PAPERS/MOPRI103.pdf.

J.R. Greening, B.Sc., "The Determination of X-Ray Energy Distributions by the Absorption Method"; Physics Department, Westminster Hospital, London, S.W.1; vol. XX, No. 230; pp. 71-78; Feb. 1947.

S.A. Ogorodnikov et al., "Application of High-Penetrating Introscopy Systems for Recognition of Materials"; 7th European Particle Accelerator Conference, Vienna, Austria, Jun. 26-30, 2000, pp. 2583-2585; Available at http://accelcont.web.cem.ch/AccelConf/e00/PAPERS/WEP6B12.pdf.

V.L. Novikov et al.; "Dual Energy Method of Material Recognition in High Energy Introscopy Systems", Proc. 16. International Workshop on Charged Particle Linear Accelerators, Alushta, Crimea, Ukraine, 1999, pp. 93-95, appeared in ISSN 1562-6016. Available at http://vant.kipt.kharkov.ua/ARTICLE/VANT_1999_4/article_1999_4_93.pdf.

M.F. Vorogushin et al; "Experiments on Material Recognition for 8 MeV Customs Inspection System for Trucks and Large-Scale Containers"; Proceedings of the XXth International Linac Conference held Aug. 21-25, 2000 in Monterey, CA; pp. 642-644; Available at http://www.slac.stanford.edu/econf/C000821/TUE13.pdf.

* cited by examiner

```
                          ... PIXEL X
                 6.1   6.0  / 6.0
   FIG. 3  ...   5.8  | 5.9 |  6.1  ...
                 6.0   5.8    6.0
                        ...
```

```
                          ... PIXEL X'
                 2.5   2.3  / 2.2
        ...      2.3  | 2.4 |  2.4  ...    FIG. 4
                 2.3   2.3    2.5
                        ...
```

|     |     |     |     |     | ... | PIXEL A |     |     |     |
|-----|-----|-----|-----|-----|-----|---------|-----|-----|-----|-----|
| 6.0 | 6.1 | 6.7 | 6.3 | 7.0 | 8.1 | 7.9 | 7.9 | 7.9 | 7.6 | 6.9 |
| 5.4 | 4.0 | 4.0 | 4.0 | 4.0 | 4.0 | 4.0 | 4.0 | 4.0 | 4.0 | 7.3 |
| 4.9 | 4.0 | 4.0 | 4.0 | 4.0 | 4.0 | 4.0 | 4.0 | 3.8 | 4.0 | 7.1 |
| 4.8 | 4.0 | 4.0 | 4.0 | 4.0 | 4.0 | 4.0 | 4.0 | 4.0 | 4.0 | 7.0 |
| 4.8 | 4.0 | 4.0 | 4.0 | 2.4 | 2.6 | 2.7 | 4.0 | 4.0 | 4.0 | 7.0 |
| ... 5.1 | 4.0 | 4.0 | 4.0 | 2.5 | 2.5 | 2.5 | 4.0 | 4.0 | 4.0 | 6.9 ... |
| 5.1 | 4.0 | 4.0 | 4.0 | 2.6 | 2.5 | 2.4 | 4.0 | 4.0 | 4.0 | 6.8 |
| 5.3 | 4.0 | 3.9 | 4.0 | 4.0 | 4.0 | 4.0 | 4.0 | 4.0 | 4.0 | 7.1 |
| 5.1 | 4.0 | 4.0 | 4.0 | 4.0 | 4.0 | 4.0 | 4.0 | 3.7 | 3.7 | 7.3 |
| 5.3 | 4.0 | 4.0 | 4.0 | 4.0 | 4.0 | 4.0 | 4.0 | 4.0 | 4.0 | 7.1 |
| 5.2 | 5.4 | 5.4 | 5.9 | 5.8 | 5.7 | 5.8 | 5.9 | 5.7 | 5.7 | 6.1 |

MATRIX B9  MATRIX B3  PIXEL B

| 2.7 | 2.9 | 3.5 | 3.4 | 3.0 | 2.9 | 2.5 | 2.4 | 2.4 |
|-----|-----|-----|-----|-----|-----|-----|-----|-----|
| 2.7 | 2.6 | 2.5 | 2.7 | 3.4 | 3.1 | 2.8 | 3.5 | 3.5 |
| 2.9 | 2.8 | 2.9 | 2.8 | 2.4 | 2.7 | 2.9 | 3.0 | 3.1 |
| 2.5 | 2.4 | 2.2 | 2.5 | 2.4 | 2.7 | 2.8 | 2.8 | 2.9 |
| 2.6 | 2.5 | 2.5 | 2.5 | 2.5 | 2.6 | 2.7 | 2.7 | 2.8 |
| 2.7 | 2.7 | 2.9 | 2.9 | 3.0 | 3.0 | 3.0 | 3.1 | 3.1 |
| 2.8 | 2.9 | 3.0 | 3.0 | 3.1 | 3.2 | 3.1 | 3.1 | 3.0 |
| 3.1 | 3.0 | 3.2 | 3.2 | 3.3 | 3.3 | 3.2 | 3.2 | 3.0 |
| 3.3 | 3.3 | 3.4 | 3.4 | 3.4 | 3.5 | 3.3 | 3.2 | 3.1 |

FIG. 11

DUAL ENERGY RADIATION SCANNING OF CONTENTS OF AN OBJECT BASED ON CONTENTS TYPE

FIELD OF THE INVENTION

Radiation scanning of objects, including large objects such as cargo containers, to identify contraband.

BACKGROUND OF THE INVENTION

The smuggling of contraband, such as guns, explosives, drugs, as well as weapons of mass destruction, onto planes in carry-on bags and in luggage, as well as across borders and by boat in large cargo conveyances, such as cargo containers and pallets, is an ongoing concern.

Weapons of mass destruction that may be smuggled in cargo conveyances and smaller objects, include nuclear devices, such as atomic bombs and "dirty bombs," which use a conventional explosion to disperse radioactive material over a wide territory. Radioactive, fissionable, fissile, and fertile materials that may be used to manufacture atomic devices, may also be smuggled in such objects. Fissile materials, such as uranium-235, uranium-233, and plutonium-239, may undergo fission by the capture of a slow (thermal) neutron. Fissionable materials include fissile materials, and materials that may undergo fission by capture of fast neutrons, such as uranium-238. Fertile materials may be converted into fissile materials by the capture of a slow (thermal) neutron. Uranium-238 and thorium-232, for example, may thereby be converted into plutonium-239 and uranium-233, respectively. Fissionable, fissile, and fertile material are referred to herein as "nuclear material."

Radiation is commonly used in the non-invasive inspection of contents of objects, such as luggage, bags, briefcases, cargo containers, and the like, to identify hidden contraband at airports, seaports, and public buildings, for example. For example, in a line scanner, an object to be inspected is passed between a stationary source of radiation, such as X-ray radiation, and a stationary detector. The radiation is collimated into a fan beam or a pencil beam. Radiation transmitted through the object is attenuated to varying degrees by the contents. The attenuation of the radiation is a function of the density of the materials through which the radiation beam passes. The transmitted radiation is detected and measured. Radiographic images of the contents of the object may be generated for inspection. The images show the shape, size and varying densities of the contents.

The stationary source of radiation used in a common inspection system is typically a source of X-ray radiation of about 160 KeV to about 450 KeV. The X-ray source may be a source of Bremsstrahlung radiation, for example. The X-ray source in this energy range may be an X-ray tube. Objects may be scanned at more than one energy in the KeV range to obtain additional information concerning the material content of the object.

Standard cargo containers are typically 20-50 feet long (6.1-15.2 meters), 8 feet high (2.4 meters) and 6-9 feet wide (1.8-2.7 meters). Air cargo containers, which are used to contain a plurality of pieces of luggage or other cargo to be stored in the body of an airplane, may range in size (length, height, width) from about 35×21×21 inches (0.89×0.53×0.53 meters) up to about 240×118×96 inches (6.1×3.0×2.4 meters). Large collections of objects, such as many pieces of luggage, may also be supported on a pallet. Pallets, which may have supporting side walls, may be of comparable sizes as cargo containers and use of the term "cargo conveyance" encompasses cargo containers and pallets. X-ray radiation of 450 KeV will not completely penetrate large objects such as cargo containers. MeV (megavoltage) X-ray sources are required.

It has been found to be difficult to distinguish nuclear devices and nuclear materials from other dense items that may be contained within a cargo container by standard X-ray scanning. It has been suggested that additional information may be derived about the material composition of the contents of objects by X-ray scanning at multiple energies in the MeV range. For example, two X-ray beams with energy spectra may be provided by X-ray sources with accelerating potentials of 6 MV and 9 MV or higher, which generate X-ray radiation beams with peak energies of 6 MeV and 9 MeV, respectively. For an X-ray beam having a peak energy of 6 MeV, the X-ray radiation will be attenuated mainly by Compton scattering. There is not much pair production over most of that spectrum. For an X-ray beam having a peak energy of 9 MeV or higher, more pair production is induced. Compton scattering also takes place. A ratio of the transmitted radiation detected at two energy endpoints may be indicative of the atomic numbers of the material through which the radiation beam passes. Although pair production starts at 1.022 MeV, Compton scattering predominates until higher peak energies are reached. An example of such a process is described in U.S. Pat. No. 5,524,133, for example, where a ratio of the mean number of X-rays detected at each energy endpoint by the detector array as a whole for each slice or by the individual detectors of the array is determined and compared to a look up table to identify a mean atomic number corresponding to the ratio. The material content of the freight is thereby said to be determined.

However, as is known in the art, dual energy techniques that seek to determine the effective atomic numbers or identities of materials, are not effective in the MeV range. (See, for example, "Better Imaging: The Key to Better Cargo Inspection," Moore, John F., et al., Port Technology International 2001, 10$^{th}$ ed., Vol. 4, 113-119; and "Processing of interlaced images in 4-10 MeV dual energy customs system for material recognition," Ogarodnikov et al., Physical Review Special Tropics—Accelerators and Beams, Vol. 5, 104701-1-104701-11 (2002) ("Ogarodnikov")). As described in more detail in the Background of U.S. Pat. No. 7,257,188 B2, a parent of the present application which is incorporated by reference herein, multiple measurements of X-ray attenuations through the same material have a statistical distribution with a high standard deviation. Therefore, determinations of effective atomic numbers and the actual identities of materials under examination by such measurements, in a reasonable period of time for commercial applications, suffer from high false positive rates. Ogarodnikov describes a dual energy technique, apparently using a ratio of effective absorption coefficients, averaged over a Bremsstrahlung spectrum, to generate a color image of a scanned cargo container. Different colors indicate that material is in one of up to four material groups—organic, organic-inorganic, inorganic, or heavy substances, using segmentation techniques.

The accuracy of a scanning system seeking to identify a material, such as uranium, for example, may be characterized by its "sensitivity" and its "specificity". Sensitivity is the probability that the presence of uranium in a cargo conveyance will be identified. A system with high sensitivity will identify more true positives (correct identification of the presence of uranium) and fewer false negatives (missed detection of uranium) than a system with low sensitivity. However, increased sensitivity may result in an increase in the number of false positives, which may not be acceptable. Specificity, which is a statistical measure of accuracy, is the probability that the scanning system will properly identify the absence of uranium in a cargo conveyance, for example. A system with high specificity will identify fewer false positives (identification of uranium in a cargo conveyance when it is not present), than a system with low specificity.

SUMMARY OF THE INVENTION

Fissionable, fissile, and fertile materials ("nuclear materials") have high atomic numbers (Z). For example, uranium has an atomic number ("Z") of 92 and plutonium has an atomic number of 94. Special Nuclear Material ("SNMs"), which more readily undergo fission than other fissile materials, are defined by the U.S. Nuclear Regulatory Commission to include plutonium, uranium-233, and uranium enriched in the isotopes of uranium-233 or -235. Radioactive materials, certain of which may have lower atomic numbers than nuclear materials (cobalt-60, for example, has an atomic number of 27), are typically shielded by high atomic number materials, such as lead (Z=82), tungsten (Z=74), and palladium (Z=46). Iron, which is a main material in a majority of industrial goods shipped in cargo conveyances, in contrast, has an atomic number of 26. Agricultural goods, which may also be shipped in cargo conveyances, have even lower atomic numbers. Agricultural goods are predominantly composed of carbon (Z=6), nitrogen (Z=7), and water ($H_2O$, H (Z=1); O (Z=8)), which have even lower atomic numbers.

U.S. Pat. No. 7,257,188 B2 ("the '188 patent"), U.S. Patent Publication No. 2008/0205594 A1, U.S. Patent Publication No. 2007/0210255, and U.S. Pat. No. 7,423,273, which are assigned to the assignee of the present invention and application and are incorporated by reference herein, describe, in part, examination of the contents of objects for the at least potential presence of high atomic number materials that may be indicative of the presence of nuclear materials. It is noted that while the '188 patent will be referred to below, all of these patents and applications have substantially the same disclosure. The high atomic number materials may be materials having atomic numbers greater than a predetermined atomic number. The predetermined atomic number may be the atomic number of iron or the atomic number of oxygen, for example, and may depend on the expected contents of the object being examined. The predetermined atomic number may be the atomic number of other elements, as well, as discussed below. Objects themselves and objects buried underground may be examined, as well.

In one example, the contents of an object are examined by scanning the object with two radiation beams having different peak energies, detecting the radiation, calculating a function of the radiation detected at the two energies, and determining whether the object at least potentially comprises a material having an atomic number greater than a predetermined atomic number based, at least in part, on the function. The object may be a cargo conveyance and both energy endpoints may be greater than 1 MeV, for example. The energy endpoints may be 9 MeV and 5 MeV, for example.

The function may be a ratio between the radiation detected at the two energy endpoints, for example. Such a ratio is referred to herein as a transmission ratio ("TR"). Material having an atomic number greater than the predetermined atomic number is referred to as high atomic number material ("HANM"). The first function may be compared to a second function that is based, at least in part, on the predetermined atomic number, to make the determination. The second function may be a threshold, for example. The threshold may be based, at least in part, on a ratio (also a TR) derived from scanning a test material having the predetermined atomic number, at the same two energy endpoints, for example. The threshold may be further adjusted by a predetermined integral or non-integral number of standard deviations. Varying the number of standard deviations will affect the sensitivity and specificity of the system, typically in opposite directions. For example, increasing the number of standard deviations may improve the specificity, decreasing the number of false positives, but it may also decrease the sensitivity, decreasing the detection of true positives. Specificity and sensitivity need to be balanced in a particular application.

Functions may be calculated between radiation detected at each energy, for corresponding portions of the object. A projection of a portion of the radiation beam transmitted through a particular portion of the object, onto a surface, such as a detector, is referred to as a "pixel." The corresponding portions may be corresponding pixels. Corresponding pixels preferably overlap by at least one-half, but that is not required. The projection of the corresponding pixels onto the surface is referred to as "resultant" pixels or just pixels.

Resultant pixels meeting the test criterion are at least potentially indicative of an HANM in the associated region of the object. To improve the specificity and sensitivity of the conclusion that HANM is present, different types of resultant pixel groupings may be analyzed, in different ways. For example, a grouping may be formed about each suspect resultant pixel (a resultant pixel that meets the test criterion), or a plurality of groupings may be formed to encompass all pixels in an array. Multiple tests may be conducted.

Thresholds may be selected based on the material content of the cargo conveyance, which is identified in the manifest for the cargo conveyance. However, the manifest may be mistaken or incomplete. An incorrectly declared manifest may cause selection of thresholds that does not reflect the contents of the container and are therefore less sensitive and/or less specific than desirable. This may result in a higher false alarm rate than desired, or missed detections. Nuisance alarms may also be increased if HANM that are not threats but are not properly identified on the manifest, are identified by the test procedure. In addition, the accumulated attenuation of the other material in a cargo conveyance, such as agricultural material, might interfere with the reliable identification of a small amount of HANM.

Embodiments of the present invention help compensate for errors in the manifest and the attenuation of background material. In accordance with one embodiment of the invention, a method of examining contents of an object is disclosed comprising scanning the object at least one radiation energy and detecting the radiation after interaction with the object. The method further comprises determining whether the contents of the object comprise organic or inorganic material based, at least in part, on the detected radiation and at least one preliminary test criterion adapted to differentiate between inorganic material and organic material. The method further comprises determining whether the object at least potentially contains high atomic number material having an atomic number greater than a predetermined atomic number based, at least in part, on the detected radiation and whether the contents comprise organic or inorganic material. At least one organic based test criterion or at least one inorganic based test criterion may be selected based, at least in part, on the determination and it may be determined whether the object at least potentially contains high atomic number material having an atomic number greater than a predetermined atomic number based, at least in part, on the detected radiation and the at least one selected test criterion.

The at least one preliminary test criterion may comprise at least one high sensitivity test criterion representative of organic material, such as plastic or water, for example, or may be based, at least in part, on a material having an atomic number less than the atomic number of iron and greater than the atomic number of oxygen. Determining whether the contents comprise organic or inorganic material may comprise detecting radiation at two different energies after interaction with a portion of the object and calculating a first function of the detected radiation at the two different radiation energies for the portion, comparing the first function to the at least one preliminary test criterion, and determining whether the contents of the object comprise organic or inorganic material based, at least in part, on the first function and the comparison.

Determining whether the object comprises organic or inorganic material may further comprise calculating a plurality of first functions for a respective plurality of portions, comparing respective first functions to the at least one preliminary test criterion, grouping the first functions into at least one group, calculating at least one second function for each of the at least one groups based, at least in part, on the first functions in the at least one group meeting the at least one preliminary test criterion, and determining whether the object at least potentially contains inorganic material or organic material based, at least in part, on the at least one second function of the at least one group.

The at least one organic based test criterion and the at least one inorganic based test criterion may each comprise test criterion sets comprising a plurality of test criterion. For each first function, one of the plurality of test criteria may be selected based, at least in part, on the radiation detected at least one of the radiation energies. Each first function may then be compared to the respective selected test criterion.

Determining whether the object at least potentially comprises high atomic number material having an atomic number greater than a predetermined atomic number may comprise calculating at least one third function of the detected radiation at the two different radiation energies for at least a portion of the object, comparing the at least one third function to the at least one selected test criterion, and determining whether the object at least potentially comprises high atomic number material based, at least in part, on the comparison. The calculated at least one third function may be the same as the at least one calculated first function, in which case, the method comprises comparing the calculated at least one first function to the selected test criterion.

A plurality of third functions may be calculated, the plurality of third functions may be grouped into at least one second group, at least one fourth function may be calculated based, at least in part, on the third functions in the at least one group meeting the at least one selected test criterion, and the determination of whether the object at least potentially contains high atomic number material may be based, at least in part, on the at least one fourth function. The at least one first group of first functions and the at least one second group of third functions may be the same size.

In accordance with a related embodiment, a method of examining contents of an object is disclosed comprising scanning an object with at least one radiation beam, detecting the radiation after interaction with the object, and determining whether the object at least potentially contains high atomic number material having an atomic number greater than the predetermined atomic number based, at least in part, on the detected radiation and at least one high sensitivity test criterion of a first type based, at least in part, on a first predetermined atomic number representative of inorganic material, or at least one high sensitivity test criterion of a second type based, at least in part, on a second predetermined atomic number representative of organic material. The method further comprises classifying a type of background material proximate the at least potential high atomic number material as either inorganic material or organic material based, at least in part, on the detected radiation, and, if the type of test criterion matches the type of background material, confirming that the object at least potentially comprises high atomic number material.

If the type of test criterion and the type of the background material do not match, the method may further comprise normalizing the radiation detected through the at least potential high atomic number material for the presence of the background material, and selecting at least one second test criterion of the same type as the at least one first test criterion and having greater specificity to high atomic number material than the at least one first test criterion. The method further comprises confirming that the object at least potentially contains high atomic number material based, at least in part, on the normalized detected radiation and the at least one second test criterion.

If the type of test criterion and the type of background material do not match, the method may further comprise selecting at least one second, high sensitivity test criterion of a type matching the type of the background material, and confirming that the object at least potentially comprises high atomic number material based, at least in part, on the detected radiation and the second test criterion.

The type of background material may be classified based, at least in part, on the detected radiation and at least one preliminary test criterion adapted to differentiate inorganic material from organic material.

The method in accordance with this embodiment may include additional aspects of the method of the first embodiment.

In accordance with another embodiment of the invention, a system for examining contents of an object is disclosed comprising at least one radiation source to scan an object at least one radiation energy, at least one detector to detect radiation after interaction with the object, at the at least one radiation energy, and a processor configured to determine whether the contents of the object comprise organic or inorganic material, and determine whether the object at least potentially contains high atomic number material having an atomic number greater than a predetermined atomic number based, at least in part, on the detected radiation and whether the contents comprises organic or inorganic material. The processor may be further configured to operate to implement the additional aspects of the methods of the first and second embodiments, described above, and herein.

The term "radiation energy" refers to an energy characteristic of the radiation beam. The characteristic may be the energy endpoint or peak energy of the beam, for example. The radiation energy may also refer to an average or nominal value of the energy of the beam. Other characterizations of the energy of the beam may be used, as well.

BRIEF DESCRIPTION OF THE DRAWINGS

FIG. 3 is an example of an array of values of X-ray radiation of 9 MeV transmitted through a portion of a cargo conveyance, at a plurality of pixels;

FIG. 4 is an example of an array of values of X-ray radiation of 5 MeV transmitted through the portion of the cargo conveyance of FIG. 6, at a plurality of pixels;

FIG. 5 is an example of an array of transmission ratios ("TRs") for a group of resultant pixels based on the X-ray radiation measured in FIGS. 3 and 4;

FIG. 11 is an example of an array of TRs for a group of pixels representing a portion of a cargo container;

DESCRIPTION OF THE PREFERRED EMBODIMENTS

In accordance with embodiments of the invention, test criterion, such as thresholds and threshold sets, for use in analyzing detected radiation after scanning of an object, such as a cargo conveyance, are selected based on the type of the contents of the object. The radiation may be detected at two different energies. The contents of the object may be determined by radiation scanning the object and analyzing the detected radiation with appropriate criterion. Appropriate material based criterion can then be used in the dual energy tests described in U.S. Pat. No. 7,527,188 B2 ("the '188 patent"), which is incorporated by reference herein, or other such tests. Before describing the embodiments of the present invention, the dual energy tests and radiation scanning systems described in the '188 patent, and the theory behind dual energy tests, will be described in detail.

Iron has an atomic number ("Z") of 26. Since typical items in a cargo conveyance comprise iron and other materials with atomic numbers less than iron, the presence of any material having an atomic number greater than iron is suspicious. It is therefore sufficient to screen for HANMs, without identifying the particular material (although that is an option). While some HANM may not be nuclear materials, non-nuclear HANMs, such as lead (Pb, Z=82), tungsten (W, Z=74), and bismuth (Bi, Z=83) may be used to shield nuclear materials, and are, therefore, also suspect materials. The presence of legitimate HANMs in cargo conveyances and the like is rare, and when they are present, they should be identified on a manifest for the cargo conveyance. Silver (Ag, Z=47), for example, has medical, industrial, and photographic uses. If silver is being shipped for such legitimate uses, it should be identified on the manifest. In addition, nuclear material may be distinguished from other HANM by their transmissions and shapes in an image. Checking the manifest and visually inspecting an X-ray image of the cargo conveyance may thereby avoid identification of the HANM as a nuclear material, decreasing the incidence of false positives.

In the '188 patent, which is incorporated by reference herein, experiments demonstrating that ratios of transmissions through different materials at different energies enables classification of materials as HANM, are described in detail. The following is a brief description of those experiments.

Samples of iron, lead, lucite, and tungsten were scanned with radiation beams having nominal energies of 9 MeV (measured half value layer ("HVL") 1.16 inches, 2.95 cm) and 5 MeV (HVL 1.04 inches, 2.64 cm). The energy transmission for each image was computed by dividing a histogram mean of the image by a histogram mean of an image at the same energy without the sample present, to normalize the image. A ratio of the energy transmissions at 8.5 MeV to 4.5 MeV were then calculated and recorded. The transmission at 8.5 MeV was also recorded.

Figure 1A:
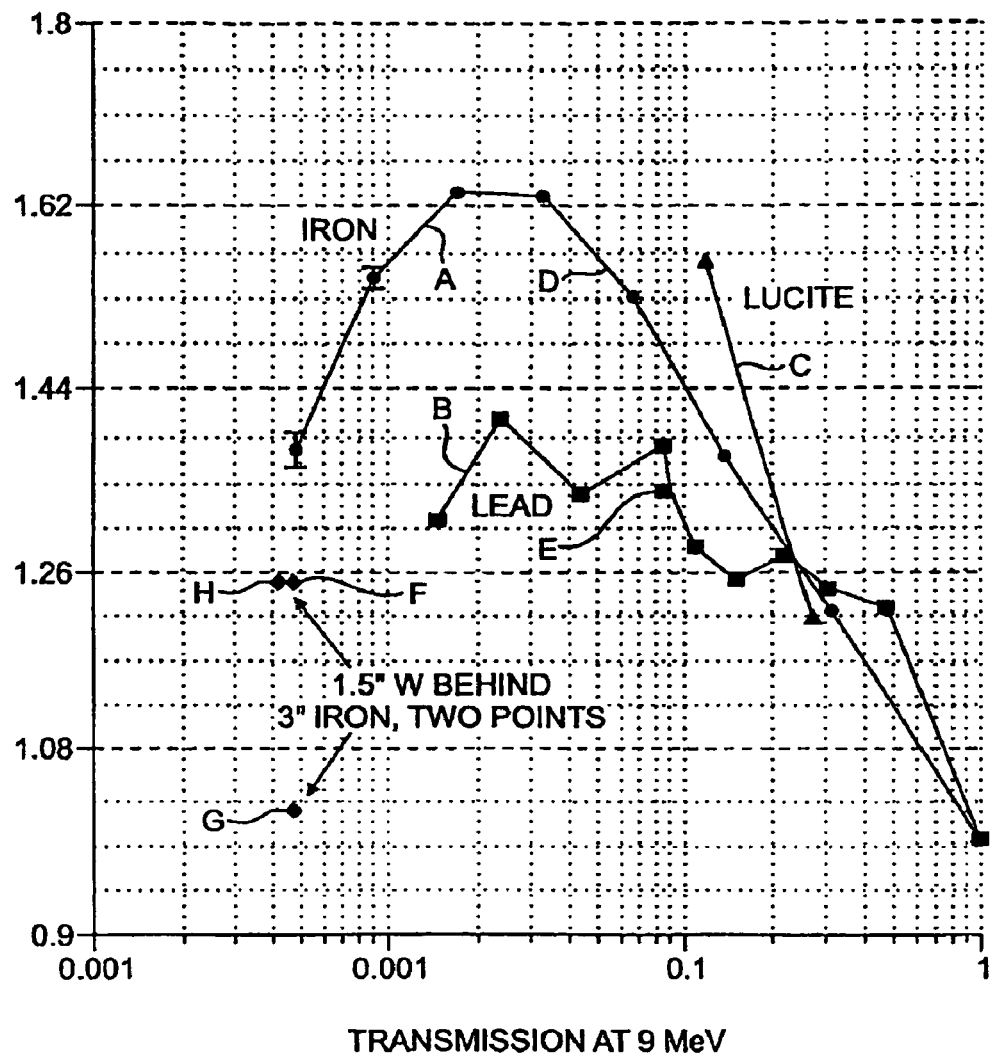
FIG. 1a is a graph of measurements of transmitted radiation at 9 MeV and 5 MeV as a function of transmitted radiation at 9 MeV, for a variety of materials.

The results are shown in FIG. 1a, which is a graph of the ratio of the transmission of a radiation beam having a nominal energy of 9 MeV to the transmission of a radiation beam having a nominal energy of 4.5 MeV, along the Y axis, versus the transmission at 8.5 MeV, along the X axis. The X axis is semi-logarithmic. Curve A is a guide to the eye connecting calculated ratios at different transmissions, which correspond to different thicknesses of the sample, for iron. Curve B connects calculated ratios at different transmissions for lead. Curve C connects calculated ratios at different transmissions for lucite. Point D shows the ratio for iron next to tungsten. Point E shows the ratio for lead next to iron. Point F shows the ratio for transmission through 1.5 inches (38.1 mm) of tungsten behind 3 inches (76.2 mm) of iron. Point G shows the ratio for 1.5 inches (38.1 mm) of tungsten behind 3 inches (76.2 mm) of iron in a different image. Point H shows the ratio for 3 inches (76.2 mm) of lead behind 3 inches of iron (76.2 mm).

The curves and points in FIG. 1a show good separation between materials at low transmission (high attenuation). Iron, lead, and lucite may be clearly distinguished at transmissions of about 0.1 and less, as can tungsten and lead behind iron. In addition, the position of the curves with respect to each other shows that the ratios for materials decrease as the atomic number increases, in this example. Materials may therefore be classified as HANM based on the ratios for each material and comparison to a respective ratio to a ratio of iron, for example. It is noted that the curves converge as complete transmission (X=1) is approached.

Figure 1B:
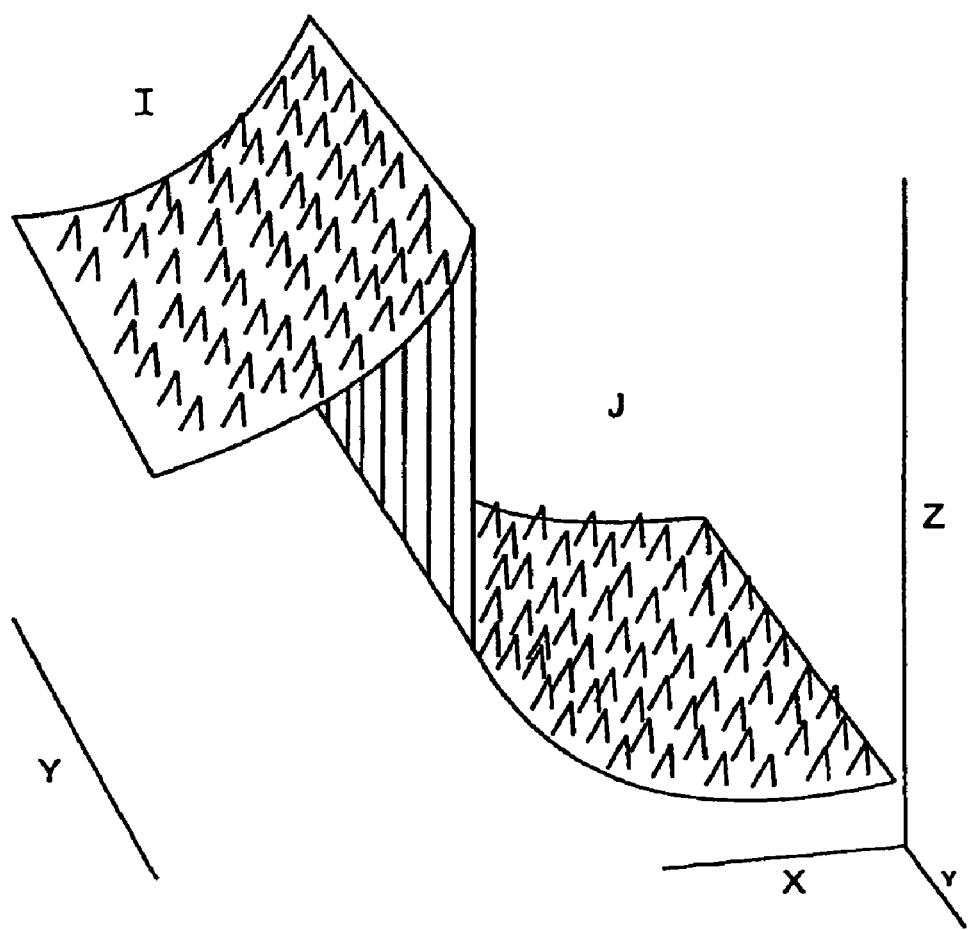
FIG. 1b shows a surface plot of ratios of transmitted radiation at 9 MeV to 5 MeV, through a piece of iron adjacent to a piece of lead.

FIG. 1b is a surface plot of a ratio image between transmission at 8.5 MeV and transmission at 4.5 MeV through 3 inches (76.2 mm) of steel (iron) adjacent to 1.5 inches (38.1 mm) of lead. Different thicknesses are used so that the transmission is the same through both materials. Portion I of the image is that of steel (iron) and portion J of the image is that of lead. The steel (iron) and lead have about the same energy transmission at 8.5 MeV, as measured by the detector. The ratios are significantly different. The two materials may be readily distinguished because their ratios are separated by many standard deviations. Where the transmission is lower, the standard deviations will be larger, the ratios will be closer together, and more sophisticated statistical analysis would be required.

Figure 1C:
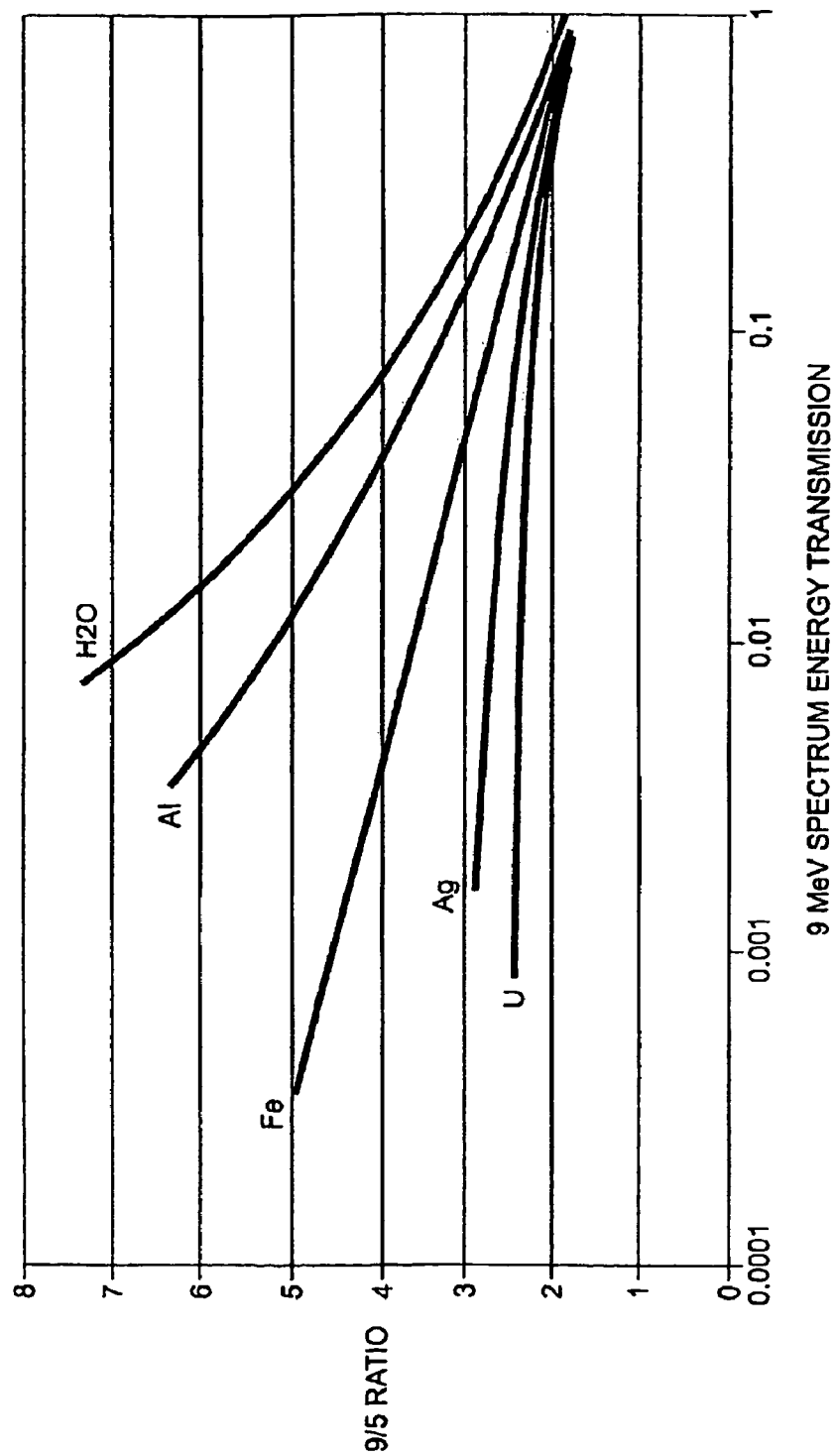
FIG. 1c shows five curves representative of ratios of simulated measurements of transmitted radiation at 9 MeV and 5 MeV as a function of transmitted radiation at 9 MeV, through identified materials.

FIG. 1c shows five curves depicting simulated ratios of radiation transmitted through five (5) different materials (water ($H_2O$), aluminum, iron, uranium, and gold), as indicated, at 9 MeV to transmitted energy at 5 MeV, as a function of the energy transmitted at 9 MeV, based on a simulation without these problems. The curves are smoother than in the test above, and converge as transmission at 9 MeV increases. As above, at high attenuation of the incident radiation (low transmission), there is significant separation among the different materials. The separation, which increases as transmission decreases (attenuation increases), shows a dependence on atomic number. In addition, the ratio decreases as the atomic number increases, in this example. If the ratio was calculated by dividing the lower energy by the higher energy, then the ratio would increase as the atomic number increases.

Without being limited to any particular theory, it is believed that the relationship between the ratio and the atomic number results from the differential effects of Compton Scattering and pair production at different energies. With low atomic number materials (such as aluminum (Z=13) and water ($H_2O$, H (Z=1), O (Z=8)), Compton scattering is the dominant mechanism at high energies, such as 9 MeV. Compton scattering causes the low atomic number materials to scatter lower energy photons, such as 5 MeV photons, at a higher rate than they scatter higher energy photons, such as 9 MeV photons, which increases the ratio of transmitted radiation for low atomic number materials. For higher atomic number materials, such as silver (Z=47) and uranium (Z=92), pair production causes removal of the high energy photons, thus reducing the ratio. In addition, the variation of the ratio is less sensitive to changes in energy transmission, resulting in a nearly flat curve as energy transmission increases.

In FIGS. 1a and 1c, if iron (Fe, Z=26), which has the highest atomic number among materials commonly found in cargo conveyances, is used as a test material, calculated ratios less than the ratio of iron is indicative of the presence of a material having an atomic number greater than iron. As discussed above, typical items in a cargo conveyance comprise iron and other materials with atomic numbers less than iron. The presence of any material with an atomic number greater than iron is, therefore, suspicious.

FIGS. 1a and 1c also show that as the energy transmission increases (because the materials are thinner), the difference between the ratios for different materials decreases. While FIGS. 1a and 1c show greater differences between the ratios for different elements and substances as energy transmission decreases (for thicker objects), it is noted that as the energy transmission gets smaller, fewer photons per pixel may be detected. This may increase the error margin of the measured ratio, decreasing the accuracy with which materials may be differentiated. The '188 patent, which is incorporated by reference herein, account for the noisy data statistically.

In the '188 patent, the relationship between the ratio of transmission or attenuation of radiation through a material at two different energies and the atomic number of the material is used to determine whether an object at least potentially contains materials having atomic numbers greater than a predetermined atomic number, which is considered to be a high atomic number material ("HANM"). The predetermined atomic number is selected so that the HANM may be a nuclear material or shielding for a nuclear material.

In one example, an object is scanned with at least two different X-ray energy distributions or spectra having different maximum energy levels, which is also referred to as endpoints or peak energies. Examples of energy distributions that may be used include 5 MeV and 9 MeV, 1 MeV and 9 MeV, and 5 MeV and 15 MeV. The radiation transmitted through the object at the two different energy endpoints is measured by detector elements of a detector array. Radiation may also be detected at each energy end point after being transmitted through the air just before an object enters the respective radiation beam, for example, for use in normalization. Normalization for air transmission is optional. Each detector element receives radiation along a beam path through portions of the object, from the X-ray source to a detector element. A projection of the radiation transmitted along each beam path, onto a surface, is referred to as a "pixel." The surface may correspond to all or a part of a receiving surface of the detector array, which may be flat or curved, for example, as is known in the art. Each pixel may correspond to one or more detector elements of the detector array. If an image is generated, which is an option but is not required, the pixels may correspond to pixels of the image.

A function of the detected radiation at the two different energy endpoints for corresponding portions or pixels is calculated. "Corresponding" portions or pixels result from the same or substantially the same beam path through the object. Since the object is typically being moved across a radiation beam during scanning, the object may be moved a slight distance between scanning at the first and second energy endpoints. Corresponding pixels may not, therefore, be derived from exactly the same beam path through the cargo conveyance. Preferably pixels are considered to be "corresponding" if their respective beam paths through the cargo conveyance overlap by at least one-half, although that is not required. For example, the pixels may overlap by less than half. It will be apparent to those skilled in the art that in certain cases, such as if less sensitivity and specificity may be tolerated, corresponding pixels may be proximate to each other (within a few pixels of each other) and need not overlap.

As discussed above, the function may be a ratio between the radiation detected at the higher energy endpoint (such as 9 MeV) and the radiation detected at the lower energy endpoint (such as 5 MeV), or vice versa, for example. Such a ratio is referred to as a transmission ratio ("TR"). To calculate the TR in one example, transmitted radiation detected at the higher energy endpoint is divided by transmitted radiation detected at a lower energy endpoint for a plurality of corresponding pixels. TRs for the corresponding pixels, referred to as "resultant pixels" or just pixels, may be represented as an array or a matrix of numbers (corresponding to the ratios) associated with the positions of respective resultant pixels. Instead of measuring radiation transmission, radiation attenuation may be measured and used in the ratio. Other functions may be used, as well. For example, an asymmetric parameter function may be used, such as a ratio between: 1) the energy detected at a first energy endpoint plus the energy detected at a second energy endpoint, and 2) the energy detected at the first energy endpoint minus the energy detected at the second energy endpoint. In other words, (detected radiation at 9 MeV+detected radiation at 5 MeV)÷(detected radiation at 9 MeV−detected radiation at 5 MeV), or vice-versa.

In the '188 patent, the TRs of resultant pixels are compared with a second function based on a test material having the predetermined atomic number (above which materials are considered to be HANM). Potential HANM are identified based, at least in part, on whether the TRs meet criterion with respect to the second function. The second function may be a threshold, for example, and the criterion may be whether the TR is above or below the threshold. The threshold may be determined by calculating an average of the TRs of the transmitted radiations at the same two energy endpoints as is used by the system to scan an object under inspection, for the resultant pixels of the test material. All resultant pixels may be analyzed or a statistically sufficient number of resultant pixels may be analyzed to characterize the test piece. Preferably, the average TR is adjusted by an integral or non-integral number of standard deviations of the TRs, to achieve a desired sensitivity and specificity. It is also preferred to calculate the average TR for different thicknesses of the test piece. Since transmission varies with thickness, particular thresholds may thereby be calculated and used for particular transmissions or range of transmissions detected at each pixel. The transmission at the higher energy endpoint, here 9 MeV, may be used to select the threshold. The transmission at 5 MeV may be used, instead.

Preferably, the test material has an atomic number equal to or greater than known the highest atomic number of acceptable materials. For example, radioactive materials, such as uranium (Z=92) and plutonium (Z=94), are of particular concern because they can undergo self-sustaining fission reactions. The test material, therefore, preferably has an atomic number less than the atomic number of uranium. As mentioned above, lead (Z=82), tungsten (Z=74), and bismuth (Z=83) are also of concern because they may be used to shield radioactive material. More preferably, the test material therefore has an atomic number less than tungsten. It is even more preferred that the test material be iron (Z=26), which is the highest atomic number material commonly found in cargo conveyances and luggage in significant quantities. Copper (Z=29) and nickel (Z=28), which have atomic numbers close to iron, may also be used. If the cargo conveyance or other such object contains agricultural products, which may be determined based on a manifest for the cargo conveyance, for example, then a threshold based on a test piece of a plastic, such as Lucite® or Delrin®, may be used. Iron, copper, nickel or other materials having atomic numbers less than the materials of concern may be used in the analysis of cargo conveyances containing agricultural goods, as well.

The result of the comparison of the TR of the pixels to the threshold is indicative of whether the atomic number of the material in the volume of the object traversed by the radiation beam is above or below that of the material of the test piece. In the case where the TR is calculated by dividing a value of a high energy pixel by a value of a corresponding low energy pixel, if the TR is less than the threshold, then the volumes traversed by the radiation beams resulting in those pixels at least potentially comprise material having a higher atomic number than the material of the test piece and is identified as at least a potential HANM. Materials below that atomic number are classified as non-HANM. In the case where the TR is calculated by dividing the value of a low energy pixel by the value of a corresponding high energy pixel, if the TR is greater than the threshold, then the volumes traversed by the radiation beams resulting in those pixels at least potentially comprises material having a higher atomic number than the material of the test piece and is identified as at least a potential HANM. It is noted that in accordance with embodiments of the invention, it is not necessary to identify the atomic number of the material.

Figure 2:
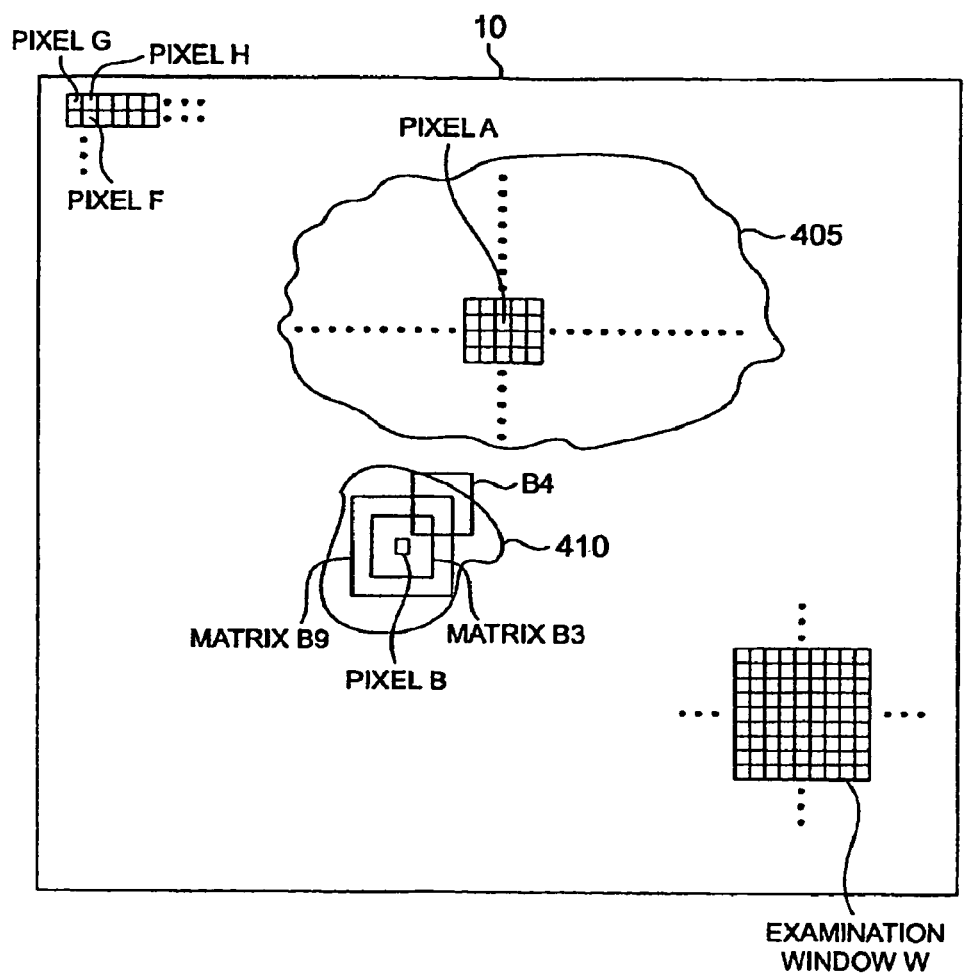
FIG. 2 is a schematic representation of an example of a portion of an X-ray image of a cargo conveyance.

FIG. 2 is an image 10 of a portion of cargo conveyance containing an item 405, an item 410, and selected pixels, including illustrative pixels A, B, F, G, and H. The pixel A lies within the item 405. The pixel B lies within the item 410. An examination window W, discussed in detail below, is also shown. The size of the pixels may depend on the size and/or number of detector elements comprising the detector, imaging integration time, etc. The smallest pixel size may correspond to a single detector element or number of detector elements. In one example, the size of each detector element and each pixel is 0.5 cm×0.5 cm.

If the radiation beam used to scan the cargo conveyance 10 is a vertical fan beam, FIG. 2 is representative of a combination of a plurality of adjacent vertical, one dimensional scanning arrays resulting from scanning the cargo conveyance. If the radiation beam is a cone beam, FIG. 2 is representative of one or more two-dimensional scanning areas resulting from scanning the cargo conveyance 10.

The values of the transmitted radiation detected at these and other pixels are stored as arrays in memory of a scanning system for processing by a processor, such as a computer. FIG. 3 is an example of a portion of an array of values of radiation energy detected at a plurality of pixels for radiation of 9 MeV transmitted through a portion of a cargo conveyance. FIG. 4 is an example of a corresponding array for radiation detected at corresponding pixels for radiation transmitted through the cargo conveyance at 5 MeV through the corresponding portion of a cargo conveyance. For example, at 9 MeV, the normalized transmitted radiation detected at the pixel X is $5.9\times10^{-3}$ and at 5 MeV, the transmitted radiation detected at the pixel X' is $2.4\times10^{-3}$. Since all measurements of transmitted radiation are of the same order of magnitude ($10^{-3}$), that term is omitted hereafter. FIG. 5 is an example of an array of the calculated TRs for the same portion of the cargo conveyance as FIGS. 3 and 4. The TR of a resultant pixel A resulting from dividing the value of X (5.9) by the value of X' (2.4) yielding a TR of 2.5, is shown. A resultant pixel typically has the same size and shape as the initial pixels. All of these values are hypothetical.

Figure 6A:
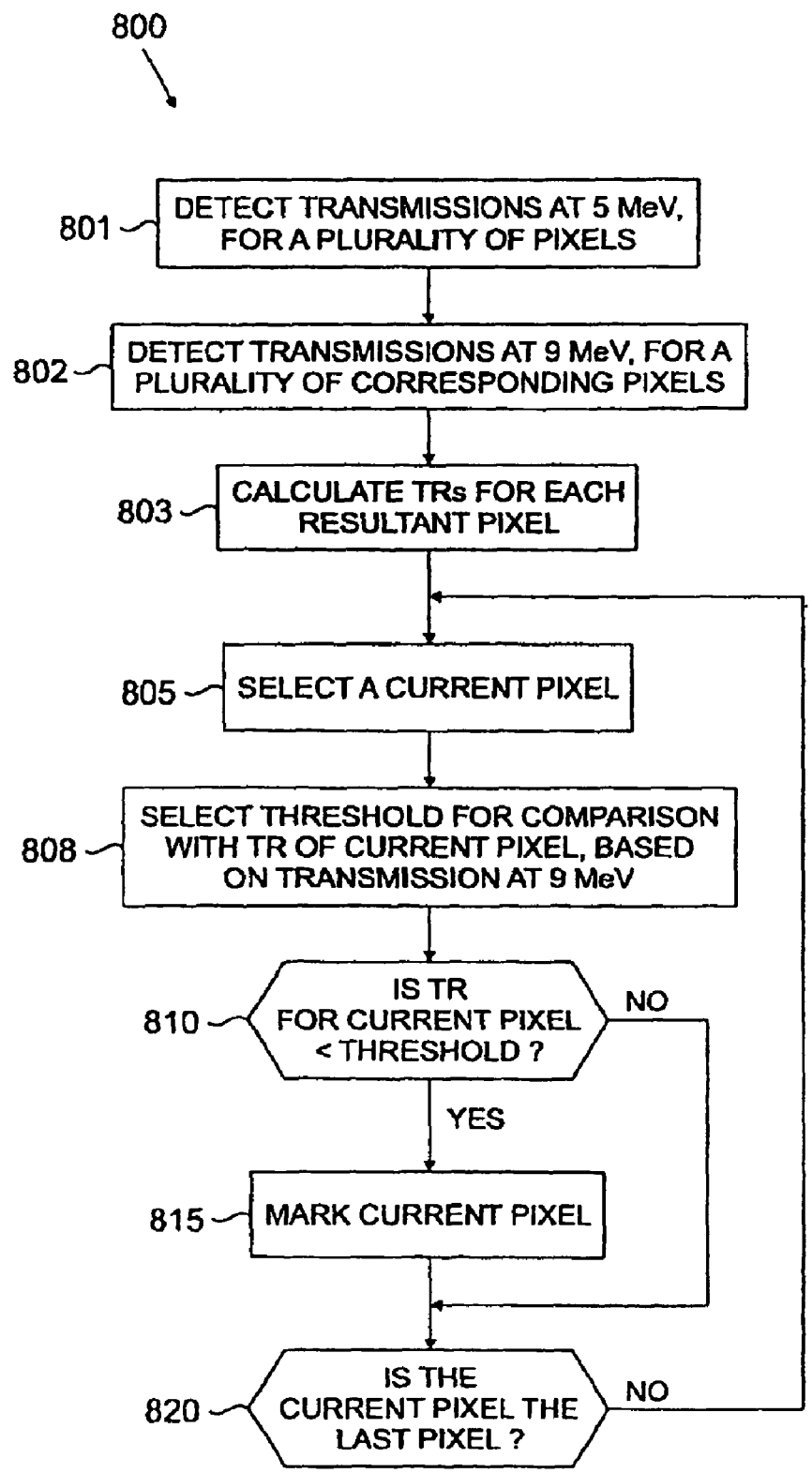
FIG. 6a is a flow chart of an example of a method for adjusting detected radiation through a dense region of an image for background.

FIG. 6a is a flowchart of an example of a method 800 for calculating and analyzing TRs that may be implemented automatically by an X-ray scanning system. In this example, transmission is detected at 5 MeV and at 9 MeV for a plurality of corresponding pixels, in Steps 801 and 802, respectively. In Step 803, the TRs for each resultant pixel are calculated by dividing the measured transmitted radiation at 9 MeV at a pixel by the measured transmitted radiation at 5 MeV at a corresponding pixel, as shown in FIG. 5. A current resultant pixel is then selected for analysis, in Step 805. In this example, the resultant pixel A is selected. A threshold for comparison with the TR of the current pixel is preferably selected based on the detected transmission at one of the energy endpoints, in Step 808. It may be necessary to calculate an applicable threshold based on interpolating stored thresholds, as is discussed further, below. In Step 808, this selection is based on the detected transmission at 9 MeV. It may be based on the detected transmission at 5 MeV, instead. The selected threshold in this example is 4.35.

It is then determined whether the TR of the current resultant pixel A is below the threshold of 4.35, in Step 810. Since 2.5 is less than 4.35, this condition is satisfied. Resultant pixel A may, therefore, be an HANM. The pixel is "marked" as a potential HANM by flagging its place in the array of FIG. 6*a*, in Step 815. It is then determined whether the resultant pixel A is the last pixel to be analyzed, in Step 820. Since there are other pixels to be analyzed, the condition is not satisfied and the method returns to Step 805 to select a new pixel for analysis, and the method continues. After the computer has completed analysis of the TRs of all the pixels, the condition in Step 820 becomes true as the current pixel is the last pixel. The processing steps of the method 800 may be conducted by a processor, such as a computer, of the scanning system.

The throughput of a scanning system may be increased by conducting a prescan by known techniques to determine whether the object contains one or more dense regions that warrant further examination. If so, one or more of the tests described herein may be conducted. If not, the object may pass through the system without further examination. The prescan may comprise scanning the object with a radiation beam having one of the energy endpoints. Use of the lower energy endpoint radiation beam is preferred because it is generally more sensitive. The results may be analyzed for radiation attenuation or transmission indicative of a possible suspect material. This may be done automatically by comparing the detected radiation or contrast with a threshold, for example. Images may be generated and visually examined, as well.

A radiation beam path intercepting an HANM will typically intercept "background" material, such as agricultural materials or manufactured goods in front of and/or behind the HANM. The sensitivity and specificity of the scanning system 100 may be improved by normalizing for the background of the suspected HANM by separately calculating the TR of each pixel of a suspected HANM embedded within the background material, based on the transmitted radiation of the background material and the transmitted radiation for a combined suspected HANM and background material occupying the same beam path. Based on image processing techniques known in the art, such as segmentation, the boundaries of dense regions indicative of a possible HANM may be identified with respect to the background. Such dense regions may be identified in a prescan of the object being examined, at one of the energy endpoints, as discussed above. Then the transmitted radiation for each pixel through a dense region may be calculated by dividing the transmitted radiation of a pixel through the dense region by the transmitted radiation through the background, at each energy endpoint. The TR for each pixel in the dense region may then be calculated by dividing the adjusted transmitted radiations at each energy endpoint, as discussed above.

In order to have comparable statistical accuracy in the TR values for the dense region and the background, the size of the background is preferably selected such that the area of the background is about equal to or is the same order of magnitude as the area of the dense region. In one example, a predetermined area, such as the surrounding 1 to 5 centimeters of the contents in each direction outside the boundaries of the dense region, may be considered background material. The TR of the background material may be an average or other mathematical function of the TRs of the pixels forming the background. The median may also be used, for example. Two annular rings may be defined around the pixels of the dense region, for example. The annular ring closest to the dense region may be separated from the boundary of the dense region by 2 to 3 pixels in each direction, for example, to account for the imprecision of determining the exact boundary of the dense region. The next ring, which may encompass the same area as the suspect HANM, may be considered to encompass background material.

Figure 6B:
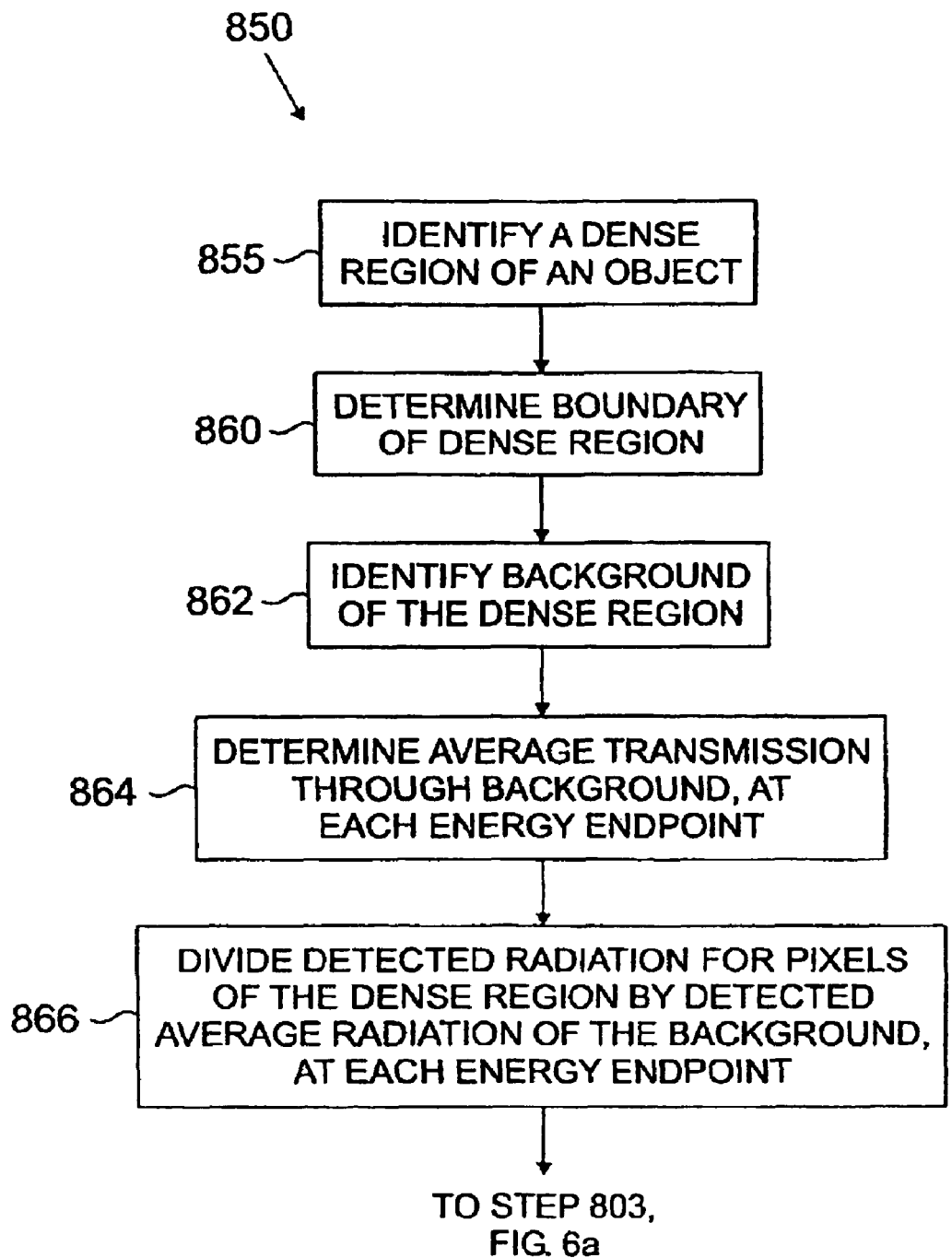
FIG. 6b is a flow chart of another example of a method to adjust detected radiation through a dense region of an image by background.

FIG. 6*b* is an example of a method 850 that may be executed by a processor, such as a computer, to adjust detected radiation through suspect dense regions of an object by the background of the dense regions. A dense region of an object is identified, in Step 855. The dense region may be identified in a prescan of the object at one of the energy endpoints, for example. The boundaries of the dense region are determined, in Step 860. Image processing techniques, such as segmentation, which are well known in the art, may be used, for example.

The background of the dense region is identified, in Step 862, and the average transmission through the background at each energy endpoint is determined, in Step 864, as discussed above. The detected radiation for each pixel of the dense region, which includes background along the beam path, is divided by the average detected radiation transmitted through the background, at each energy endpoint, in Step 866. The result is the transmitted radiation of the dense region at each energy endpoint, without the effect of the background along the beam path. The method may then proceed to Step 803 of FIG. 6*a* to calculate TRs for resultant pixels of the dense region based on the calculated transmissions for corresponding pixels, and to compare the TRs to thresholds.

The sensitivity and specificity of the determination that a low TR pixel is at least potentially indicative of an HANM based on the comparison of individual TRs to thresholds may not be sufficient for particular applications. The specificity and sensitivity of the determination that HANM is at least potentially present may be improved by grouping TRs, as described below and in the '188 patent, by increasing the number of pixels analyzed. A processor, such as a computer, of the scanning system may further analyze the resultant data, as described below.

The Examination Window Test

In one example, the number of pixels having TRs below the threshold ("low TR pixels") contained in a grouping of pixels having a predetermined area, referred to as an examination window, is examined. The examination window may be a 3 pixel×3 pixel or 9 pixel×9 pixel matrix of pixels, for example. A 9×9 pixel examination window W is shown in FIG. 2. If the number of the low TR pixels in the examination window exceeds a predetermined number, then HANM is considered to be present. The threshold value (average TR of a test piece minus/plus a value of standard deviations), the window size, and the minimum number of low TR pixels to be considered a threat may be chosen such that the probability that a non-HANM would meet the threat criterion, times the number of independent examination windows in an object (independent windows do not share common pixels) having at least one pixel below the threshold, is less than a desired sensitivity and specificity. Selection of the size of the examination window and the number of the standard deviations to be subtracted from the average TR of the test material to calculate the threshold is based on the following statistical analysis. This test is referred to as "the examination window test."

The size of the examination window may correspond to the cross-sectional area of the smallest HANM of concern that the scanning system can detect. HANM is typically smuggled in the shape of a sphere. The examination window may be the largest square fitting within a cross section of that sphere. Once the window size has been chosen, one chooses a threshold value and a minimum number of pixels below the threshold that if found will be considered a threat. Preferably, the smallest standard deviation is chosen because as the number of standard deviations increases, the probability of a response from a true HANM decreases. The threshold and minimum number are chosen such that the probability that a non-HANM will meet the detection criterion times the number of independent examination windows analyzed is less than a desired false alarm rate. An example of an acceptable false alarm rate is less than 1 in 100. Less than 1 in 1,000 is preferred. Less than 1 in 10,000 is more preferred.

In one example, a test piece of iron is scanned at the same two energy endpoints that will be used to scan cargo conveyances by that same scanning system. The TR measured at each pixel is considered to be an independent measurement of the TR for iron. For each value (integer or non-integer number) of standard deviations below the average TR of the test object, there will be a probability per pixel "p" that a single measurement will be less than the average TR minus that given value of standard deviations due to statistical fluctuations and not due to the presence of HANM. After "N" pixels are examined, there is a probability "P" that exactly "n" of these pixels will be below the threshold, also due to statistical fluctuations. This probability is given by the binomial distribution:

$$P(n \mid N) = \frac{N!}{n!(N-n)!} p^n (1-p)^{N-n}.$$

The probability of every expected outcome can therefore be calculated. Those low TR pixels that have some very small probability of occurring statistically, and therefore have a high probability of being a true HANM, may be identified. A false alarm rate, "$P_{fa}$", for a given situation is set and the probability of all the low TR pixels that would seem not to indicate the presence of a high atomic number material is evaluated. These probabilities are added until the difference between the sum and unity is less than $P_{fa}$. This sum of probabilities corresponds to the number of low TR pixels that will be false positives. Any number of low TR pixels above that corresponding number indicates the presence of a true HANM.

For example, assume a 9×9 pixel window and a threshold equal to the average TR for iron minus two standard deviations. Then the probability per pixel that a pixel is below the threshold due to statistical fluctuations is p=0.02275. The probability P(n/N) of seeing n pixels below the threshold in the 9×9 window due to statistical fluctuations is:

| n | P(n|81) | Sum of Probabilities |
| --- | --- | --- |
| 0 | 0.1550 | 0.1550 |
| 1 | 0.2923 | 0.4474 |
| 2 | 0.2722 | 0.7197 |
| 3 | 0.1669 | 0.8865 |
| 4 | 0.0757 | 0.9623 |
| 5 | 0.0272 | 0.9894 |
| 6 | 0.0080 | 0.9974 |
| 7 | 0.0020 | 0.9994 |
| 8 | 0.0004 | 0.9999 |

The probability P(n/81) that eight (8) pixels will be found below the threshold due to a statistical fluctuation is 0.0004. The sum of probabilities that eight (8) pixels will be found below the threshold due to statistical fluctuation is 0.9999. Therefore, there is a 1 in 10,000 chance that if eight (8) or more pixels are found below the threshold, it is due to a statistical fluctuation and not to the presence of HANM. This is the false negative or false alarm rate $P_{fa}$, per examination window, based on eight (8) or more pixels. The probability that nine (9) or more low TR pixels are the result of a statistical fluctuation is less than the false alarm rate $P_{fa}$ of 1 in 10,000, in this example. Therefore, to achieve a false alarm rate $P_{fa}$ of less than 1 in 10,000, per window, then 9 or more pixels with a low TR need to be found in an examination window.

Figure 7:
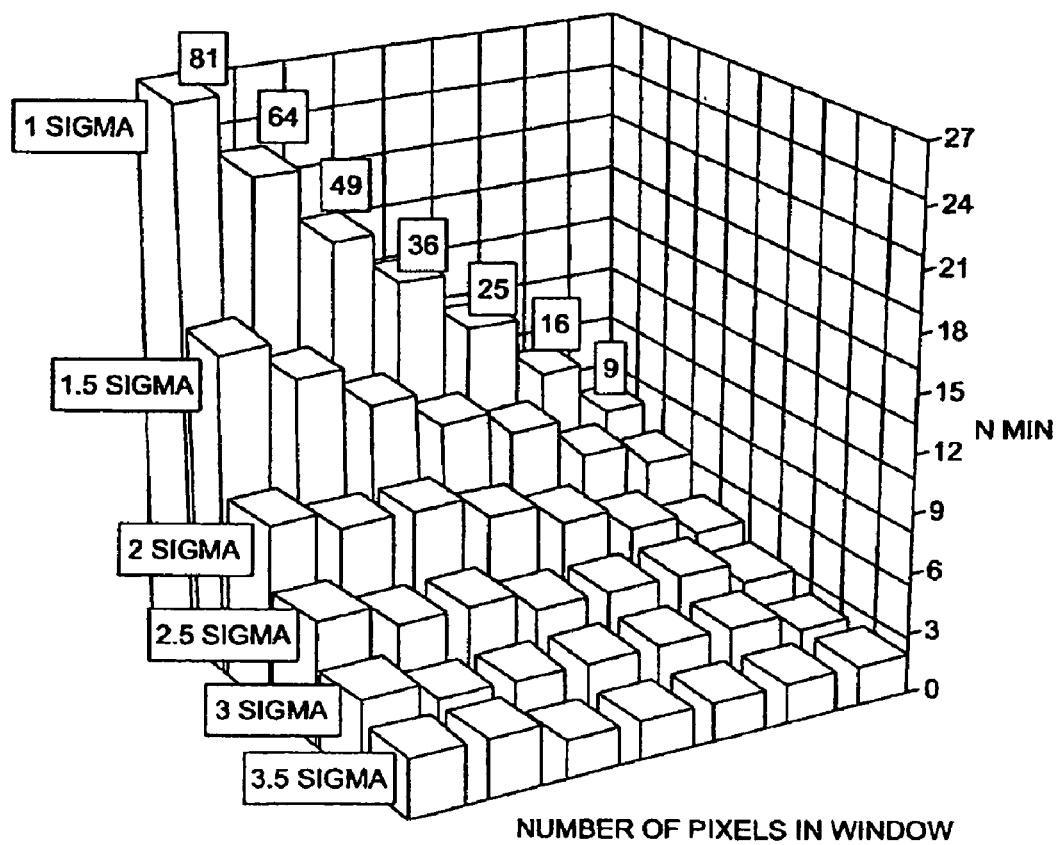
FIG. 7 is a bar chart of the minimum number of low TR pixels required to achieve a 1 in 10,000 false alarm rate for various sizes of examination windows and various standard deviations.

FIG. 7 is a bar chart of the minimum number of low TR pixels required to achieve a 1 in 10,000 false alarm rate $P_{fa}$ for various sizes of examination windows and standard deviations. If one chooses a relatively large number of standard deviations (3 or more), for example, the examination window size may be relatively unimportant because the minimum number of pixels required to indicate HANM at that false alarm rate $P_{fa}$ changes by only a small amount (a fraction of a pixel). If one uses a fairly small number of standard deviations, such as 1, then the minimum number required to indicate the presence of HANM at a particular false alarm rate $P_{fa}$ is a fairly strong function of the examination window size. For example, with a 9×9 matrix window size and 1 standard deviation, 27 pixels are required to indicate HANM with the false alarm rate $P_{fa}$ of 1 in 10,000. With an 8×8 matrix window size, 24 pixels are required.

Two examinations may be conducted, one with a larger examination window, to detect larger masses of HANM, and another with a smaller window, to detect smaller masses. As discussed above, in this system, a 9×9 matrix may be used to detect larger masses. The smaller window may be a 3×3 matrix, for example. With a 3×3 matrix, the number of standard deviations subtracted from the average TR of the test object may be 2 or 2.5, for example. At 2.5 standard deviations and a 3×3 matrix, the presence of 3 pixels below the threshold would indicate HANM with a false positive rate of 1 in 10,000, as shown in FIG. 7. The examination window test may be the sole test for determining whether an HANM is present, or it may be used in conjunction with other examination techniques, including the other examples discussed below.

The entire object may be examined by analyzing an examination window moved across the TRs of the object. For example, the window may be positioned starting in one location, such as in a corner of the object, and then moved to the opposite corner, one column of pixels at a time. Subsequently, the examination window may be moved down by one row of pixels and then across the TRs, one column of pixels at a time. The pixels in each window are analyzed and the analysis ends when all the possible examination windows of the object have been analyzed.

In an example of an implementation of the examination window test, during operation of the cargo scanning system, the cargo conveyance is subjected to two X-ray radiation beams, each with a different energy endpoint, such as at 9 MeV and 5 MeV. The radiation at each radiation endpoint is detected by a detector after interaction with the cargo conveyance. An example of a cargo scanning system that may be programmed to implement this and other tests described herein is discussed below.

Figure 8:
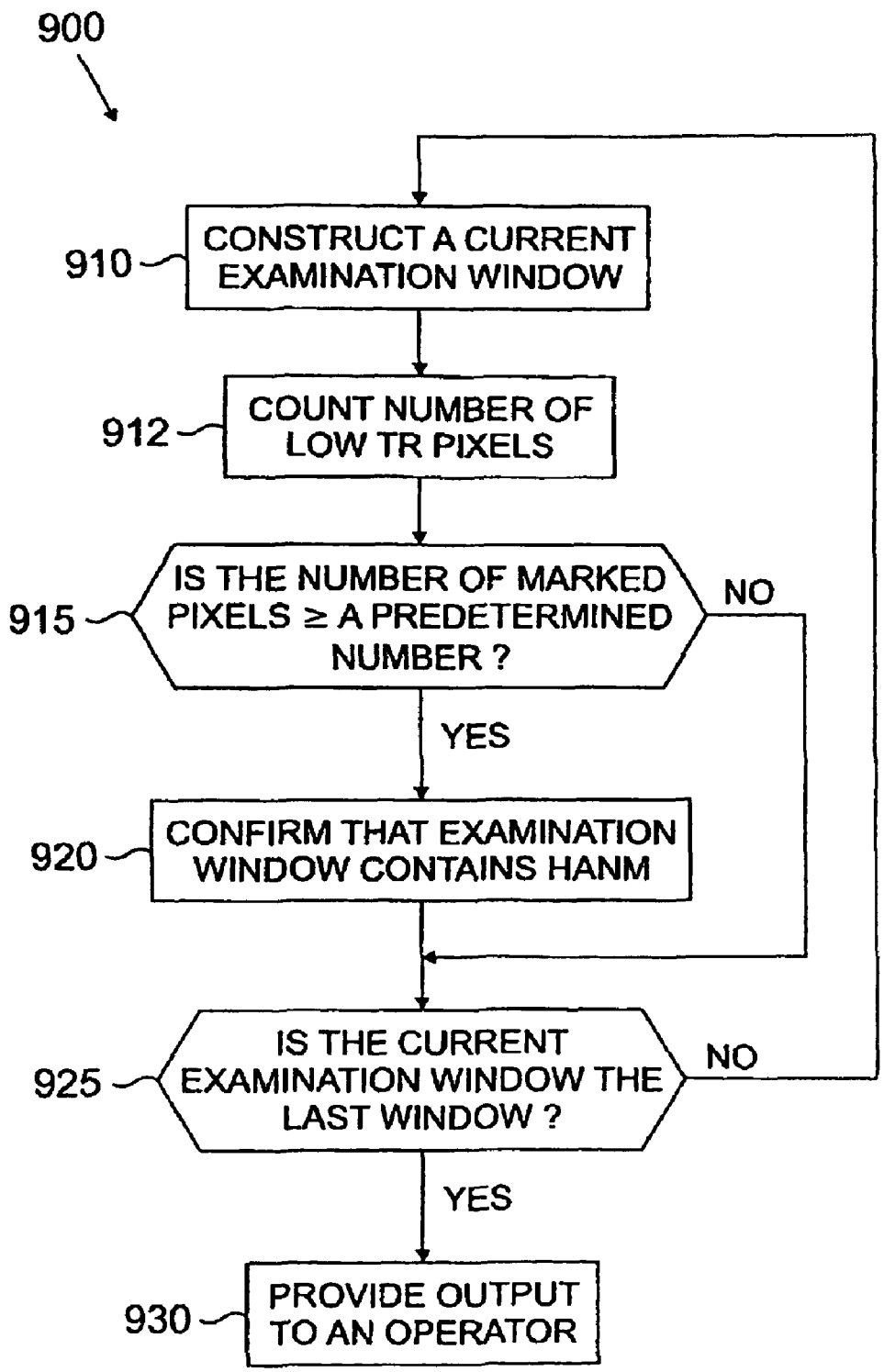
FIG. 8 is a flow chart of an example of an "examination window test;"

FIG. 8 is an example of a method 900 that may be executed by a processor, such as a computer, for example, to implement the examination window test. After calculation of the TRs of the resultant pixels, in the method 800 of FIG. 6a (and optionally in conjunction with the method 850 of FIG. 6b), for example, the computer selects a pixel and constructs an examination window, such as a 9×9 matrix, centered about the selected pixel, in Step 910. The computer identifies a number of the low TR (marked) pixels in the examination window, in Step 912, and compares it with a predetermined number, in Step 915. The predetermined number is the highest statistically determined number of low TR pixels that can be false positives (a pixel having a low TR even though the pixel is not an HANM), under the selected conditions, as discussed above. Computation of the threshold is described further below, with respect to FIG. 13, for example.

If the number of low TR pixels is greater than or equal to the predetermined number, an area of the cargo conveyance corresponding to the low TR pixels is classified as an HANM, in Step 920. If the number of the low TR pixels in the examination window is less than the predetermined number, it is determined whether the current examination window is the last examination window to be analyzed, in Step 925.

If not, the examination window is shifted one column of pixels to the left one row of pixels down, as appropriate, to construct a new current examination window, in Step 910.

Then the computer repeats all the steps of the method 900, as described above. The method 900 may be repeated with a smaller examination window, different number of standard deviations and different predetermined number. If the current examination window is the last window to be analyzed, an output is provided to an operator, in Step 930.

Figure 9:
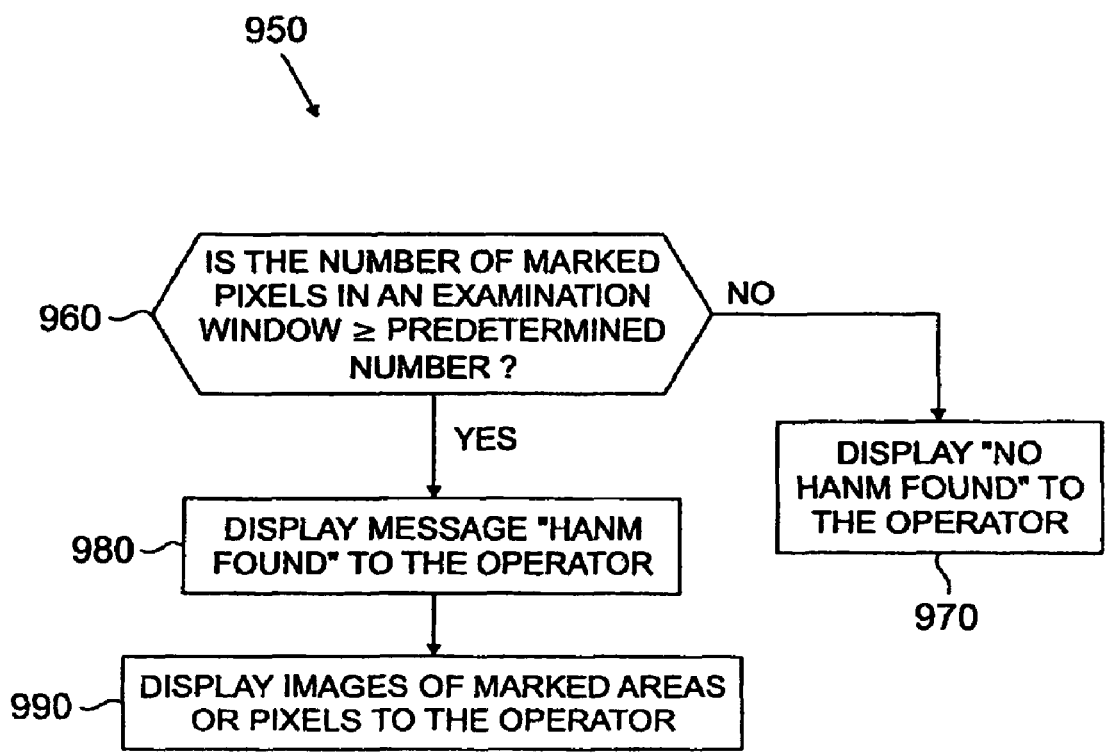
FIG. 9 is a flow chart of an example of a method for providing an output of an examination to an operator.

FIG. 9 is an example of a method 950 that may be executed by the processor, such as a computer, to display the results of the analysis to the operator of the cargo scanning system 100. In Step 960, the processor checks whether there are any examination windows with a number of marked pixels greater than or equal to the predetermined number, as determined in Step 915 of the method 900, for example. If the number of marked pixels, if any, is not greater than or equal to the predetermined number in any examination window, the processor proceeds to Step 970 and displays a message "No HANM." If the number of marked pixels in any examination window is greater than the predetermined number, the processor proceeds to Step 980 to display a message "HANM Found," for example, thus alerting the operator to the presence of a high atomic number material in the cargo conveyance. The processor may also display the images of the examination window or windows showing the presence of an HANM, in Step 990. An entire image including the windows may be displayed instead of or along with the images of the windows, as well.

If the output indicates that HANM is present, the operator may then have several options. For example, a manifest for the cargo conveyance may be checked to determine whether HANM has been properly declared and is not a threat. The HANM may be an HANM but not a radioactive material, for example, such as silver for industrial or medical use, which should be identified on the manifest. The HANM may also be a radioactive material for medical use, which should be declared on the manifest. The operator may also cause the scanning unit and the processor to perform additional scanning of the cargo conveyance and/or mathematical analysis of measurements, including other tests discussed herein, and/or the operator may conduct a manual inspection of the cargo conveyance. A cargo conveyance failing inspection due to the suspected presence of HANM may be removed from the area and dealt with in accordance with known procedures.

If the output is not indicative of the presence of HANM, the cargo conveyance may be considered to "pass" the inspection. However, if the operator still suspects HANM are present (based on the prescan, for example), the operator may still conduct a manual inspection. Also, if the method 850 of FIG. 6*b* was not used in conjunction with the calculation of TRs in the method 800 of FIG. 6*a*, the method 850 may be conducted, the TRs recalculated, and then analyzed as described above. If HANM is still not shown, any or all of the other tests described herein, or other tests known in the art, may be conducted. Once the operator is satisfied, the cargo conveyance may be "passed."

The Contiguity Test

Once a first resultant pixel meeting the test criterion is found (as described with respect to FIG. 6*a*, for example), another way to increase the number of resultant pixels analyzed is to analyze the pixel's environment to identify pixels contiguous to that pixel that also meet the test criterion. Analyzing the environment of that first resultant pixel increases the statistical accuracy (decreases the standard deviation) of the measurements because it is more likely that the first pixel is part of an HANM if contiguous pixels are also part of an HANM. Analyzing pixels surrounding the first pixel also effectively increases the number of photons contributing to a determination. If the area of the contiguous pixels is greater than or equal to a predetermined area, the identification of HANM has greater sensitivity and specificity than a determination based on a single pixel or a grouping having an area less than the predetermined area.

The predetermined area may be a cross-sectional area of the smallest HANM capable of producing a self-sustaining nuclear reaction. For example, the area may be 20.25 cm$^2$, which is the area of a 4.5 cm×4.5 cm square. A square of this size is representative of a cross-sectional area of the smallest sphere encompassing a square of these dimensions. The size of the area may be determined by counting marked pixels. (See Step 815, FIG. 6*a*, discussed above, where low TR pixels are marked.) Other smaller or larger areas may be used as well. The area of the contiguous pixels need not be in the shape of a square.

If contiguous pixels covering an area greater than or equal to the predetermined area are found, then an HANM is considered to be at least potentially present. In one example, pixels sharing an edge, such as a pixel G and a pixel H in FIG. 2, are considered to be contiguous, while pixels sharing only a vertex, such as pixels F and G, are not. A different definition of "contiguous" may be used, which may include pixels sharing a vertex, for example. This test is referred to as the "contiguity test." Comparison based on the area, rather than shape, is believed to be more reliable, but shape may be considered as well.

Figure 10:
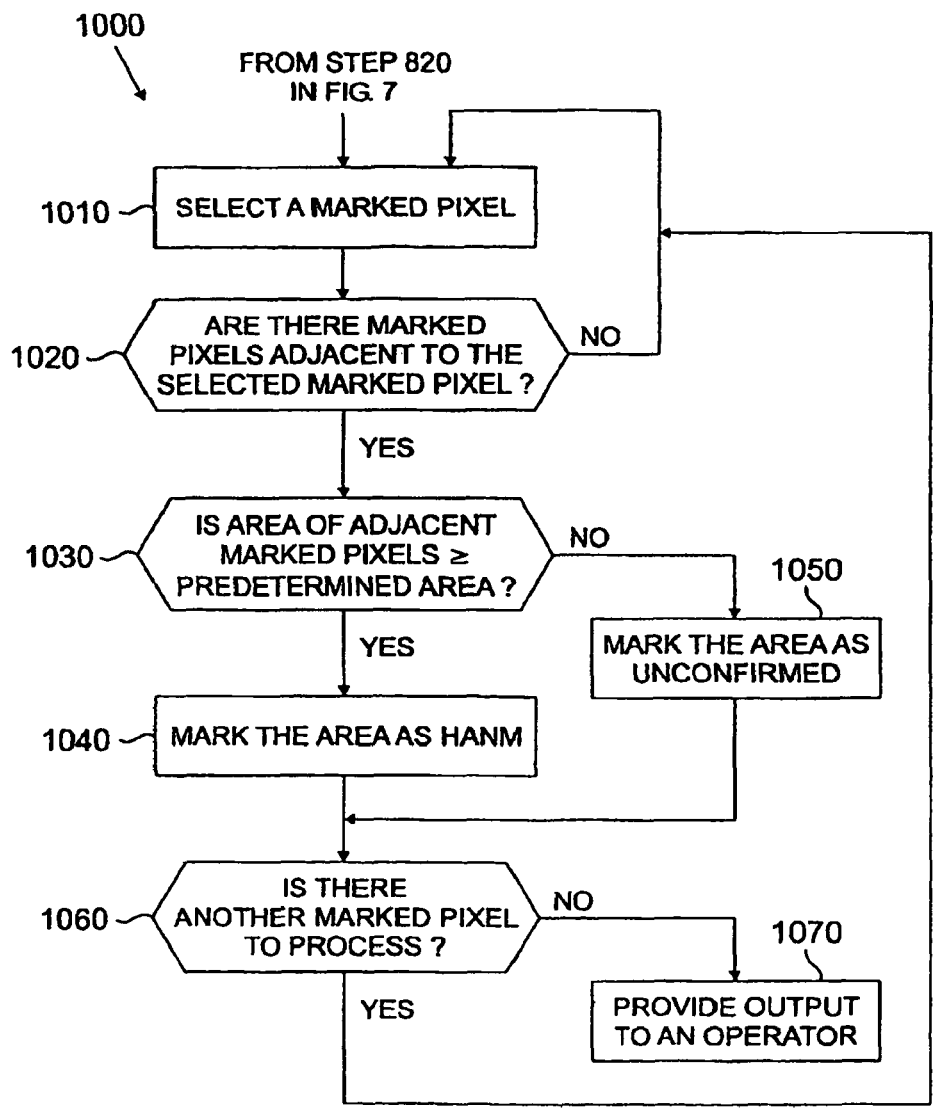
FIG. 10 is a flow chart of an example of a "contiguity test;"

FIG. 10 is an example of a method 1000 that may be executed by a processor, such as a computer, to implement the contiguity test. A marked pixel is selected, in Step 1010. It is determined whether there are additional marked pixels contiguous to the selected pixel, in Step 1020. Pixels in the array are checked and accumulated in all directions from the selected marked pixel until a first "unmarked" pixel (whose TR is above threshold) is reached in every direction. Algorithms for such analysis are well known in the art.

If there are marked pixels contiguous to the selected marked pixel, the size of the area of the contiguous marked pixels is compared to a predetermined area, such as the area of the smallest HANM the system 100 is designed to detect, in this example a 20.25 cm$^2$, in Step 1030.

The area covered by the marked pixels "accumulated" in Step 1030, is preferably determined by counting marked pixels, for example. If each pixel is 0.5 cm×0.5 cm, the area covered by 81 contiguous marked pixels centered around the pixel A shown in FIG. 5, for example, is equal to 20.25 cm$^2$ (4.5 cm×4.5 cm). While in the example the area is a square, that is not required. If the condition in Step 1030 is satisfied, the area of the contiguous marked pixels is marked as an HANM, in Step 1040. Optionally, an image of this area may be generated for display to an operator.

If the area covered by the marked pixels is less than the predetermined area, the area of adjacent marked pixels is marked as unconfirmed HANM, in Step 1050. After either Steps 1040 or 1050, it is determined whether there is another marked pixel to process, in Step 1060. If so, a new marked pixel is selected, in Step 1010, and the method 1000 is repeated. If there are no other pixels to process, then the condition in Step 1060 would not be satisfied and the computer provides an output to the operator, in Step 1070. It is noted that once an individual pixel is part of a previously marked area, it need not be further analyzed by this process (although it may be). Therefore, Step 1010 may be limited to selecting a marked pixel that is not part of a previously marked area. Step 1060 may be similarly limited to determining whether there is another marked pixel not part of a previously marked area.

The contiguity test may be used alone or in conjunction with other examination techniques, including the other examples described herein. The operator may respond to the output provided, as described above with respect to the examination window test.

Analyzing the environment of a suspect resultant pixel is also useful where only a limited number of photons may be detected at each resultant pixel. For example, certain non-threatening materials (non-HANMs), such as agricultural goods, may be very dense. Low TR pixels may be found even though the material is not an HANM, because of the low transmission through the dense material causes a high statistical inaccuracy. The contiguity test may improve the statistical accuracy of the determination based on measured radiation at a pixel by considering the radiation detected in the environment of the pixel, as well.

The Matrix Test

In another example, resultant pixels are grouped and a function of the TRs in the group is analyzed. The function may be an average or median of the TRs in the group, for example. The group may be formed about a suspect pixel or a plurality of groupings may be provided to encompass all the pixels. The grouping may be a matrix, for example. This test is therefore referred to as the "matrix test."

The item 410 in FIG. 2 is an example of another item within the cargo conveyance 10. The pixel B is a low TR, and therefore suspect pixel, within the item 410. The 3×3 pixel matrix B3 in FIG. 2 is an example of a grouping, "constructed" around the pixel B. FIG. 11 is an example of an array of the TRs for a portion of the cargo conveyance 10, showing the low TR pixel B and the matrix B3. The average TR, for example, of the matrix B3 is calculated by averaging the TRs of each pixel in the matrix. The average TR is then compared to the threshold. If the average is below the threshold, HANM may be considered to have been found. In one example, where the pixel size is 0.5 cm, the 3×3 pixel matrix B3 may be used to identify a potential HANM having a cross-sectional area of at least about 1.5 cm×1.5 cm. The threshold used in the comparison may be selected based on the average or other such function of the transmissions of the pixels in the matrix.

The statistical accuracy of the TR for the 3×3 matrix is three times greater than the statistical accuracy of the TR for the individual low TR pixel. Since false positives may cause unnecessary, costly, time consuming, and disruptive inspection of the cargo conveyance, additional confirmation, with even greater accuracy, is preferably obtained before a definitive finding is made that the pixel B belongs to an HANM.

To further improve the accuracy of the determination (to decrease the standard deviation) for larger objects, after the 3×3 matrix is examined, an even larger matrix, such as a 9×9 pixel matrix B9, which is also shown in FIG. 2 and FIG. 11, is preferably created, centered around the same selected low TR pixel B. Other size matrices, such as 5×5 and 7×7 pixel matrices, may be constructed, instead or as well. The size of the larger matrix may depend on the size of the items to be identified and the size of the pixels. The 9×9 pixel matrix B9 contains eighty-one additional adjacent pixels with data contributing to the determination of whether HANM is present. An average of the TRs of the pixels of the larger matrix is generated and is similarly compared to the threshold. If both the average TRs of the first and second matrices are below the threshold, the current low TR pixel is determined with even more confidence to represent an HANM. In this example, the 3×3 pixel matrix B3 provides a first identification of a potential HANM, whose presence is verified with greater confidence by the 9×9 pixel matrix B9.

The analysis continues until all the low TR pixels have been processed. Multiple overlapping 3×3 matrices, as well as overlapping 9×9 matrices, may be constructed across an array. FIG. 2 shows an additional 3×3 matrix B4, for example, which overlaps the matrix B3.

In another example, if the detector elements are 1.5 cm×1.5 cm and a pixel size is 1.5 cm, a 3×3 pixel matrix would encompass a 4.5 cm cube of HANM. If the detector element is 0.1 cm and the pixel size is 0.1 cm, a 45 pixel×45 pixel matrix would be required to encompass a 4.5 cm cube of HANM, or HANM covering an area of 20.25 cm.

Figure 12:
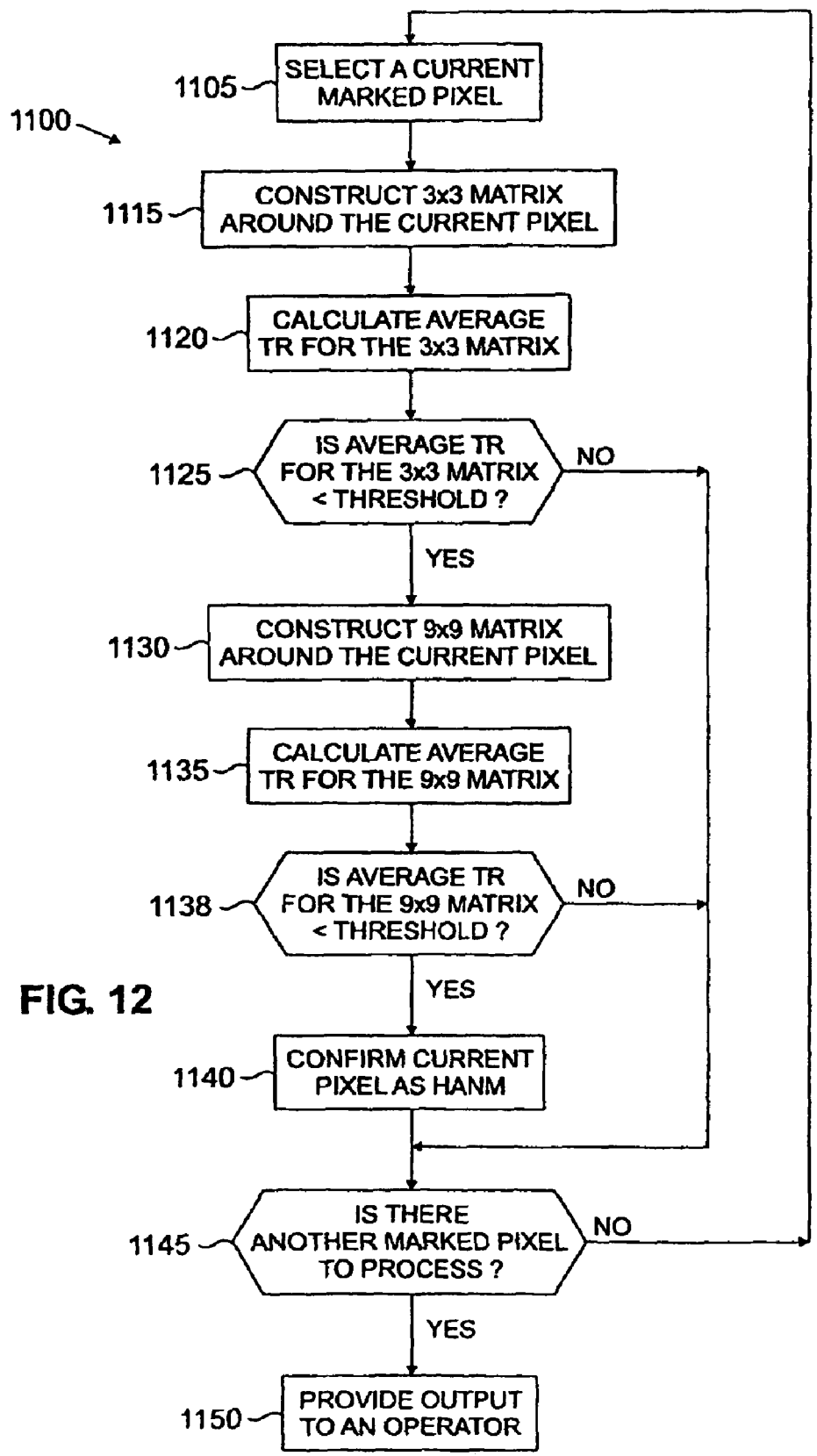
FIG. 12 is a flow chart of an example of a "matrix test," in accordance with the example of FIG. 11.

FIG. 12 is an example of a method 1100 that may be executed by a processor, such as a computer, to implement the matrix test. In this example, the pixel size is 0.5 cm×0.5 cm. After executing the method 800 in FIG. 6a to identify and mark low HANM pixels, and optionally after implementing the contiguity test, an example of which is shown in the method 1000 of FIG. 10, a current marked pixel is selected, in Step 1105. The low TR pixel B within the object 410 in FIG. 2, is selected, for example. A 3×3 matrix B3 centered around the pixel B is "constructed" (see FIG. 11), in Step 1115, to identify HANM encompassing an area of 0.5 cm×0.5 cm, and larger.

The average TR for the matrix B3 is then calculated by summing the nine TRs in the matrix B3 and dividing that sum by the number of individual pixels, in Step 1120. In this example, the average TR for the matrix B3 is 2.7. It is then determined whether the average TR of the matrix B3 is below the threshold, in Step 1125. The threshold in this example is 3.9. Since 2.7 is less than 3.9, the condition is satisfied. This means that the matrix B3 represents an HANM with an accuracy of three times that of the accuracy of the initial suspicion that pixel B may be an HANM based solely on the fact that pixel B had a low TR.

In this example, for an HANM encompassing a cross-sectional area of 4.5 cm×4.5 cm and larger, a 9×9 matrix B9 is also preferably constructed centered around the pixel B in Step 1130, to provide greater sensitivity and specificity to a finding of HANM by the 3×3 pixel matrix. An example of a 9×9 matrix B9 is shown in FIG. 12. The average TR for the matrix B9 is calculated in Step 1135. The TRs in the matrix B9 are summed and the sum is divided by 81 (the number of individual pixels). In this example, the TR for the matrix B9 of FIG. 11 is 2.9. Since nine (9) times as many pixels are considered, the statistical probability of the accuracy of the TR for the matrix B9 is three times greater than the statistical probability of the accuracy of TR of the matrix B3. The TR of the matrix B9 is compared to the threshold, in Step 1138. It is then determined whether the average TR is less than the threshold, in Step 1138. If so, then it is confirmed that the current marked pixel corresponds to an HANM, in Step 1140, with a higher degree of sensitivity and specificity. Since 2.9 is less than 3.9, the condition is met. It is then determined whether the pixel B is the last marked pixel to analyze, in Step 1145. Since there are other marked pixels to be analyzed, the condition is not satisfied, the method returns to Step 1105, and the method 1100 is repeated for the next marked pixel.

If the TR of the matrix B9 is not less than the threshold, then the pixel B is not confirmed as an HANM in Step 1140 and the method proceeds to Step 1145, as discussed above. After all the TRs of all the marked pixels are analyzed, the condition in Step 1145 becomes true and an output is provided to the operator. The operator may respond to the output as described above with respect to the examination window test.

It is believed that the matrix test may identify a cube of HANM with sides of 4.5 cm, such as an uranium cube, behind a 20 cm thick shield of iron, for example. The matrix test may be performed alone or in conjunction with any or all of the other tests described herein, or other tests known in the art. For example, if the area of the item 410 is less than the predetermined size of the contiguity test, discussed above, it would not be identified as an HANM by that test. It could still be a dangerous HANM, however, as several objects of an SNM may be smuggled in one or more cargo conveyances and combined into a single object large enough to sustain a nuclear reaction. An HANM smaller than the predetermined size could also be used in a "dirty" bomb. Items smaller than the predetermined area of the contiguity test may be identified by the matrix test using a matrix smaller than the predetermined area of the contiguity test. When the matrix test is being used to examine low TR pixels in areas less that the predetermined size of the contiguity test, only low TR pixels not part of an object greater than the predetermined size need to be selected for analysis by the matrix test, but that is not required.

It is noted that for smaller items, where only a small matrix (such as the 3×3 pixel matrix B3) encompasses enough of an item to at least potentially identify the item as an HANM, the identification of HANM may not be as reliable as if larger matrices are also used. Such potential identification may, however, justify further examination, such as conducting the other tests described herein or known in the art, checking the manifest, and/or conducting a manual examination. It is also noted that an average or other such function of TRs of groupings other than a matrix may be compared to a threshold to determine whether the grouping is at least potentially HANM. For example, the grouping may be the dense regions identified in a prescan, as discussed above. The boundaries of the dense region may be defined as discussed above, the TRs of the pixels of the dense region may be averaged, and the average compared to the threshold.

Threshold Calculation

As discussed above, the criterion for separating an HANM from a non-HANM is preferably calculated for each scanning system. Threshold calculation may take place when a cargo scanning system is periodically calibrated. The calculation depends, in part, on the desired degree of sensitivity and specificity for the system. As discussed above, the threshold may be determined by scanning a test material having an atomic number less than the lowest atomic number of a material of concern (such as uranium) at the same two energies as will be used to scan cargo conveyances. A test piece comprising a material representative of inorganic material, such as iron, nickel, and copper, for example, and a test piece comprising a material representative of organic material, such as water or a plastic such as Lucite (R) or Delrin (R), may be used, for example.

The test piece preferably has a varying thickness, so that thresholds may be calculated at different transmission through the test piece. The test piece may be wedge shaped or step shaped, for example. The thicknesses may correspond to the expected range of transmissions of acceptable materials and HANMs. Thresholds calculated at the different thicknesses may be used with the test criteria applied to resultant pixels having corresponding transmissions. The test piece may have a thickness of from about 1 mm to about 400 mm, for example. The transmission at either energy endpoint may be used. If the test piece is step shaped, the standard deviation is calculated for the TRs across each step. If the test piece is wedge shaped, the standard deviation is calculated for TRs through a particular thickness of a portion of the wedge. One or a few columns of data may be used for each thickness. This standard deviation is used during examination of an object to interpolate between measured transmissions, to calculate a threshold between calculated thresholds based on the test piece. Alternatively, the calculated threshold closest to the measured transmission may be used, but that may not be as precise.

The TRs are calculated, summed, and averaged, at each thickness. As is known in the art, the probability that a measurement is a statistical variation of a measured quantity, such as TR, is a function of the distance between the arithmetic mean of the distribution of the measurements and the measurement in question. This distance is measured in standard deviations. Such probabilities are expressed in tables and are well known in the art. For example, a measurement that is three standard deviations from the arithmetic mean of a plurality of measurements has about a 0.0013 probability of being a statistical variation. This probability is the false alarm rate, which in this example is 13 in 10,000. Therefore, to reduce the probability that the TR is a statistical variation of the actual TR with a 0.0013 probability of being incorrect, in this example three standard deviations are selected for the calculation of the threshold, at each thickness. The value of standard deviations used may be an integer, in this example, 3, or it may be a non-integer, such as 2.5, for example. The same standard deviation is preferably used at each thickness.

To achieve a different sensitivity and specificity, a different value of standard deviations may be subtracted from the average TR of the low atomic number material of the test piece, at each given that any given measurement of transmitted radiation may be from an HANM or a non-HANM, the number of standard deviations to be subtracted from the TR of a low atomic number material is selected to achieve a desired balance between an acceptable number of false positives and false negatives. For example, subtracting eight standard deviations from the TR of a low atomic number material would result in zero (0) false positives but possibly an unacceptable number of false negatives. As mentioned above, if a greater number of false positives may be tolerated, then it may not be necessary to take into consideration the standard deviation.

If the measurement at the higher energy endpoint is divided by the measurement at the lower energy endpoint, then the standard deviations are subtracted from the average TR of the test piece. If the measurement at the lower energy endpoint is divided by the measurement at the higher energy endpoint, the value of standard deviations is added to the average TR of the test piece. The specific number of standard deviations will determine the sensitivity and specificity of the systems.

Figure 13:
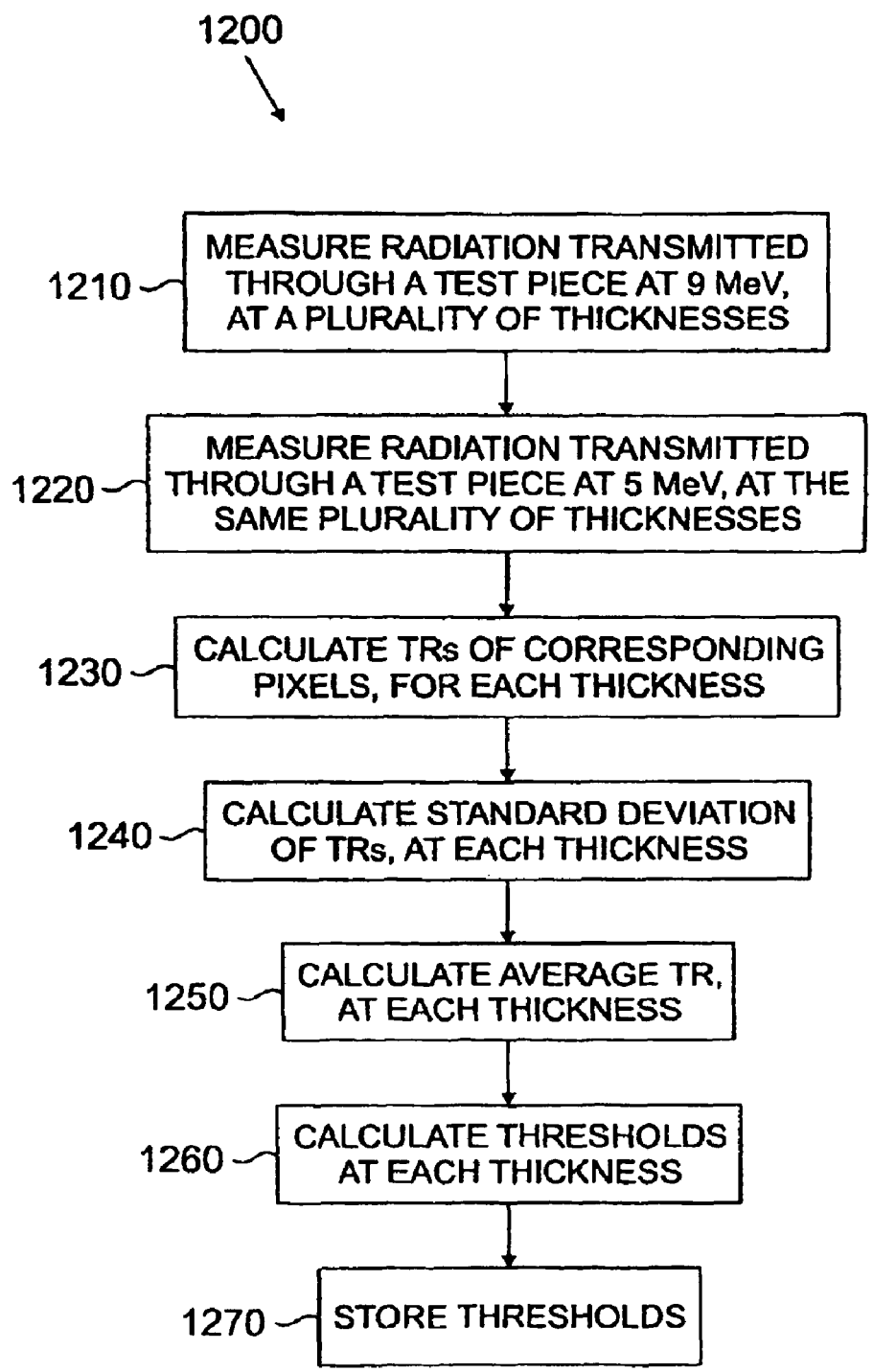
FIG. 13 is a flow chart of an example of a method for calculating thresholds.

FIG. 13 depicts an example of a method 1200 that may be implemented by a processor, such as a computer, to calculate the thresholds. A test piece is scanned by the cargo scanning system with radiation having a first, high energy endpoint, such as 9 MeV, at a plurality of thicknesses, in Step 1210. The radiation transmitted through the test piece is detected for each pixel, also in Step 1210. Scanning may be conducted at 5 MeV first, instead.

The test piece is then scanned with a second radiation beam having a second energy endpoint less than the first energy endpoint, such as 5 MeV, and the radiation transmitted through the test piece at the plurality of thicknesses is detected for a plurality of pixels corresponding to the pixels of Step 1210, in Step 1220. The TRs for resultant pixels are calculated by dividing the transmitted radiation measured at 9 MeV by the transmitted radiation measured at 5 MeV (or vice versa) for the corresponding pixels, in Step 1230.

The standard deviation of the calculated TRs is determined, in Step 1240. Preferably, the standard deviation is calculated for the TRs at each thickness of the test piece for use in interpolating between calculated thresholds during actual measurements. Standard deviation may be calculated according to the following formula:

$$S = \sqrt{\frac{\sum_{i=1}^{N}(x_i - \bar{x})^2}{N-1}},$$

where $x_i$ is the measured attenuated radiation for a pixel i, $\bar{x}$ is the arithmetic mean (average) of the measured attenuated radiation for all the pixels, which is calculated according to the formula $$\bar{x} = \frac{\sum_{i=1}^{N} x_i}{N},$$

and N is the number of pixels. In this illustrative example, the standard deviation of the test measurements of transmitted radiation is calculated to be 0.2. Other statistical methods may be used with different distributions of the measured attenuated radiation.

The average TRs of the TRs at each thickness are calculated, in Step 1250. The threshold is calculated at each thickness in Step 1260. Preferably, the thresholds are calculated by adjusting the average TR at each thickness of the test piece by an integral or non-integral number of standard deviations, dependent upon the desired sensitivity and specificity, in Step 1250. The calculated thresholds are stored, in Step 1270. Threshold sets for inorganic material and organic material may be stored in association with corresponding transmissions and standard deviations for each thickness of the test piece in a database of thresholds, for example.

Threshold Selection

It is believed that a difference of at least about 1.5 standard deviations between the TR and the test criterion, such as a threshold, for example, may be used to reliably identify the potential presence of an HANM. The cumulative attenuation of a radiation beam through a large amount of agricultural goods and a small HANM measuring 4.5 cm×4.5 cm×4.5 cm or less could result in TRs too close to the value of the iron based threshold to reliably identify the potential presence of the HANM. This can be a particular problem with an HANM with a very high atomic number, such as a SNM and tungsten. For example, using a threshold based on the average TR of iron, which may be about 4.5, to differentiate a 4.5 cm×4.5 cm×4.5 cm HANM, which may have a TR of about 2.5, embedded within a 2 meter cube of agricultural goods, which may have a TR of about 7, may be difficult due to the proximity of the TRs and the discrimination of the system.

Since an HANM typically has an atomic number that is further from the atomic number of typical agricultural goods than the atomic number of iron, it is easier to differentiate an HANM from agricultural goods than from iron with the required degree of statistical accuracy. Use of an organic threshold with organic material will therefore provide greater sensitivity to HANM, including SNM, hidden among the organic material, than if an iron based threshold is used.

Agricultural products and other types of organic materials such as gels that are transported in a cargo conveyances, such as cargo containers, typically comprise carbon (Z=6), nitrogen (Z=7), and oxygen (Z=8). Therefore, if it is known that a cargo conveyance contains agricultural products, the TR of agricultural products, or a material representative of agricultural products, such as a plastic or water, may be used in determining the test criterion, instead of the TR of iron or other such materials, as discussed above. Lucite (R) or Delrin (R) are examples of plastics that may be used. In one example, a test piece of the plastic with varying thickness may be used, as discussed above, to develop a set of thresholds, for example. The calculated test criterion, such as at least one threshold, may also be stored in the database for use in the examination techniques discussed above.

Sufficient information about the contents of the cargo conveyance to select a test criterion may be available through the customs manifest, for example. A typical manifest filed by the shipper or owner of the cargo conveyance declares the type of goods that are supposed to be shipped in the cargo conveyance, such as agricultural goods, manufactured goods, etc.

Figure 14A:
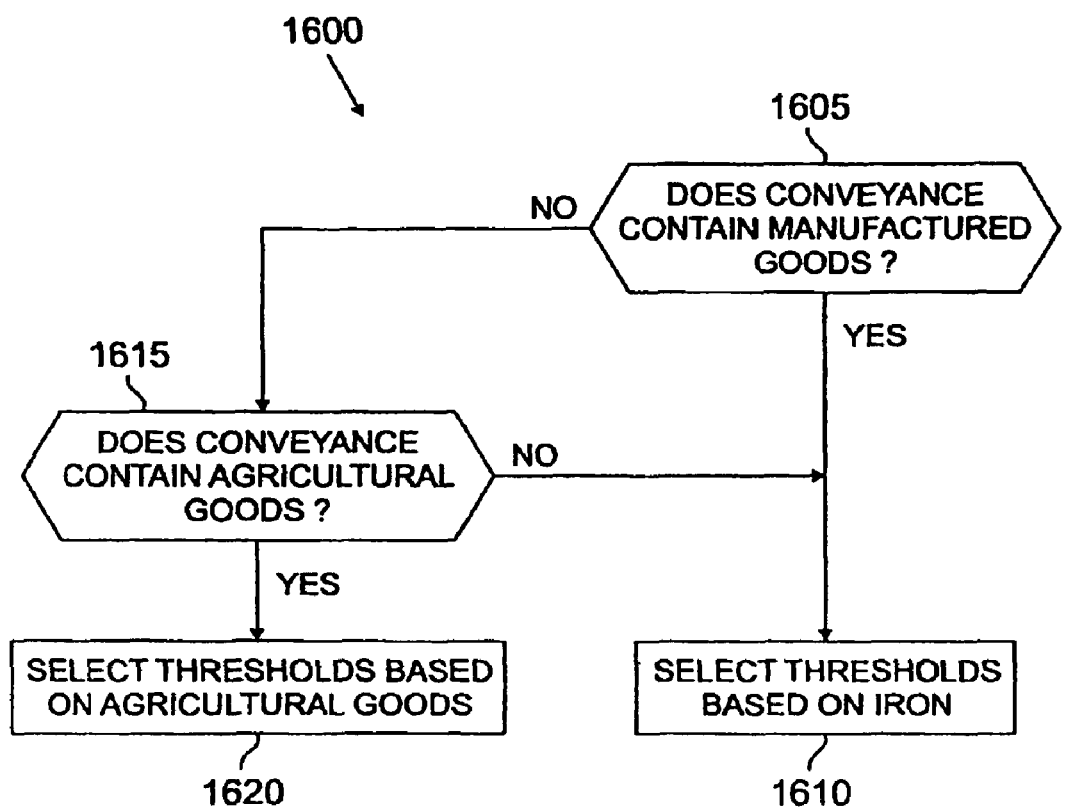
FIG. 14a is a flow chart of an example of a method for selecting a threshold based on the contents of a cargo conveyance.

FIG. 14a is an example of a method 1600 to select a test criterion, here a threshold, based on the type of contents declared in the manifest. The manifest is checked to determine if the cargo conveyance 104 contains manufactured goods, in Step 1605. As discussed above, manufactured materials typically comprise iron. If, according to the manifest, the cargo conveyance contains manufactured materials, then a threshold set based on iron is selected as the thresholds to be used in analyzing the contents of the cargo conveyance 104, as discussed above, for example, in Step 1610. A threshold set comprises a plurality of thresholds based on the same test piece material, for use at different measured transmissions. The threshold sets may be based on copper or nickel, instead. If the manifest does not indicate that the cargo conveyance contains manufactured goods, it is determined whether the manifest indicates that the cargo conveyance contains agricultural goods, in Step 1615. If it does, then a threshold set representative of agricultural goods or organic material is selected for use in analyzing the contents of the cargo conveyance, in Step 1620. The method 1600 may be implemented by an operator reviewing a manifest for the cargo conveyance being inspected. The operator may then input the thresholds, or threshold sets to be used in any or all of the tests described above, or other tests. A processor, such as a computer 2200, discussed below with respect to FIG. 16, may be configured to implement the method 1600, if the manifest has been electronically entered, for example. The processor may be configured to implement the process by hardware and/or software.

However, the manifest may be mistaken or incomplete. An incorrectly declared manifest may cause selection of a threshold set that does not reflect the contents of the conveyance and is therefore less sensitive and/or less specific than desirable. This may result in a higher false alarm rate than desired, or missed detections. Nuisance alarms may also be increased if HANM that are not threats but are not properly identified on the manifest, are identified by the test procedure.

Figure 16:
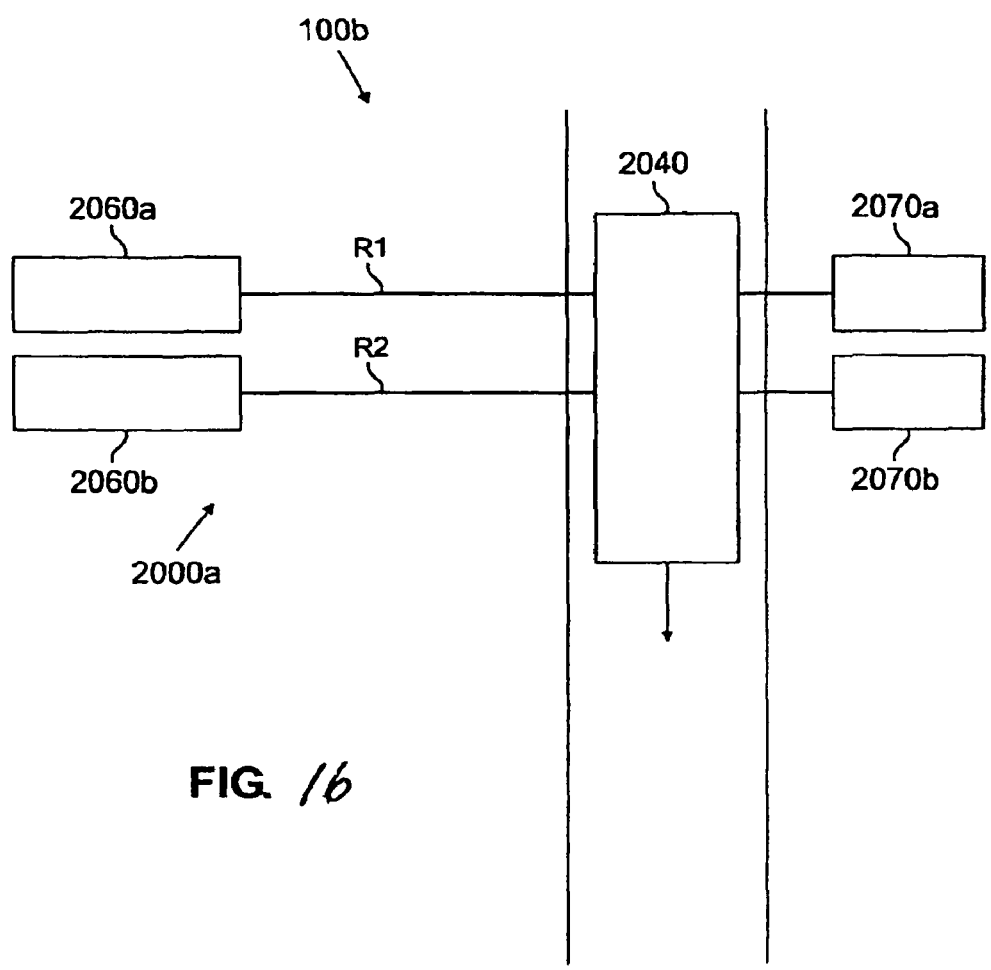
FIG. 16 is a top view of a portion of a cargo scanning system similar to the system of FIG. 15, showing two adjacent sources of X-ray radiation.

In accordance with an embodiment of the invention, one or more material based thresholds or threshold sets to be used in evaluating an object, such as a cargo conveyance, are selected automatically by a processor, such as the computer 2200 discussed below with respect to FIG. 16, based on preliminary radiation scanning of the contents of the conveyance. An appropriate threshold set for inorganic materials may be based on iron, for example, while an appropriate threshold set for organic material may be based on Lucite (R), Delrin (R), or water, for example, as discussed above.

The preliminary radiation scanning may comprise dual energy scanning by two separate radiation beams having different peak energies or one radiation beam containing a spectrum of radiation energies, as discussed herein. The detected radiation may be analyzed by any or all of the methods described above or other methods, based on a preliminary test threshold set adapted to differentiate between inorganic material and organic material. After selection of the test threshold set based on the preliminary scan and analysis, the data collected during the preliminary scan may be analyzed again using the selected threshold set. Alternatively, the cargo conveyance or a suspect portion of the conveyance may be scanned again and the detected radiation analyzed with respect to the selected test threshold set.

Since organic materials typically comprise carbon (Z=6), nitrogen (Z=7) and oxygen (Z=8), while inorganic materials transported in a cargo conveyance typically comprise manufactured products that predominantly comprise iron (Z=26), a preliminary threshold set based on a material having an atomic number between typical organic materials, such as oxygen (Z=8), and typical inorganic material, such as iron (Z=26), may be used, for example. The preliminary threshold set may be based on aluminum (Z=13), for example. A preliminary threshold set based on aluminum may be developed by use of an aluminum test piece, in the procedure described above and in FIG. 13, and stored. Other intermediate atomic number material may be used instead. Where the ratio comprises the higher energy divided by the lower energy, if the TR is less than the threshold, the conveyance contents, or contents of the conveyance in a particular area of the conveyance, at least potentially comprises inorganic material. If the ratio is greater than the threshold, the conveyance contents at least potentially comprises organic material.

The preliminary threshold set may also comprise high sensitivity thresholds based on a material representative of inorganic material, such as a plastic such as Dekin® or Lucite®, or water, for example. Thresholds having a sensitivity of at least about 80% may be used, for example. The thresholds may have a sensitivity of at least about 90%, such as about 99%, for example. The specific sensitivity used may depend on the threat level and throughput of the port or other location conducting the test, for example. Threshold calculation based on a test piece is described above.

Figure 14B:
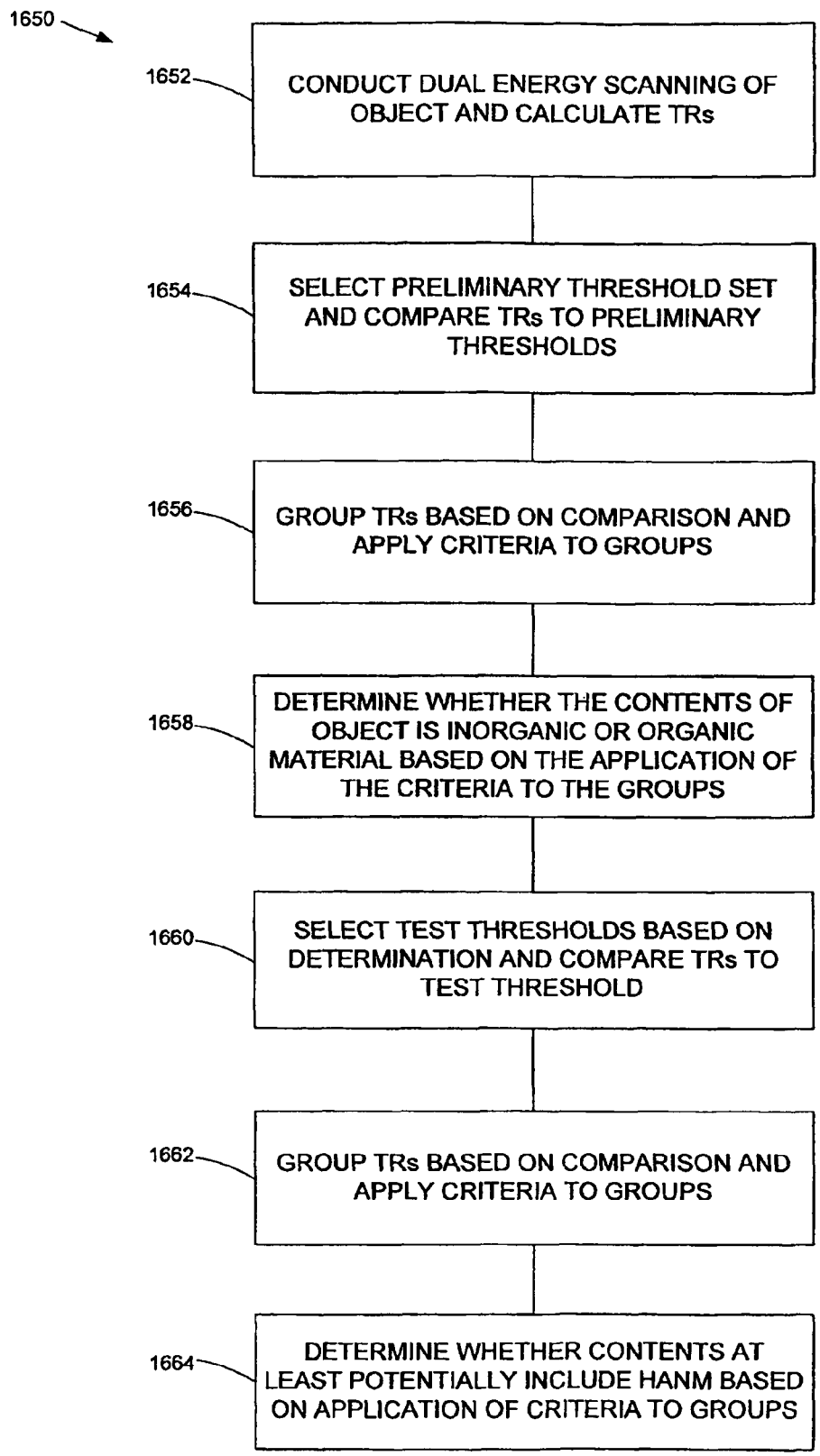
FIG. 14b is a flow chart of an example of a method for examining contents of an object in accordance with an embodiment of the invention.

FIG. 14*b* is an example of a method 1650 for examining contents of an object, such as a cargo conveyance, in accordance with an embodiment of the invention. Dual energy scanning of the conveyance is conducted and TRs are calculated, in Step 1652, as described above. The dual energy scanning may be conducted as described above with respect to Steps 801-805 of the method of FIG. 6*a*, for example.

A preliminary test criterion, such as a preliminary threshold set, is selected and each TR is compared to an appropriate threshold in the preliminary threshold set, in Step 1652, as described above with respect to Steps 805-820 of FIG. 6*a*, for example. The appropriate threshold within the selected preliminary threshold set is determined based on the transmission at one of the radiation energy levels for that portion or pixel, as described above with respect to Step 808 of FIG. 6*a*.

Based on the comparison of the respective TRs to each threshold, TRs are marked and grouped, and a function of each group is applied to preliminary test criterion, in Step 1656, as described above in more detail with respect to the methods of FIGS. 8, 10, and/or 12, for example. A function of the groups, such as a number of TRs meeting the first test criterion in a group, sizes of groups, and/or average TR of the TRs in a group, for example is determined and criteria applied to the groups. The sizes of the groups may be larger (contain more TRs corresponding to more pixels) than in the methods described above. If the groups have different sizes than the size of the groups used in the HANM test, the groups may be evaluated based on different criteria than in the corresponding HANM test described above. These criteria may be determined based on the desired sensitivity and specificity by someone of ordinary skill in the art in accordance with the teachings of the present invention.

Then it is determined whether the object at least potentially contains organic or inorganic material by the computer 2200 or other such processor, in Step 1658, based on the application of criteria to the groups in a similar manner to determining the presence of HANM in accordance with the methods of FIGS. 8, 10, and/or 12, for example. If less sensitivity/specificity is needed then grouping need not be applied. It may then be determined whether inorganic or organic material is present by comparing the number of TRs in the entire object or a portion of the object are below (or above, depending on how the ratio is calculated) the threshold to a predetermined number, for example.

An appropriate test threshold set for either inorganic or organic material is then selected by the processor 2200 from among the threshold sets stored in a memory 2202, and the TRs calculated in Step 1652 are compared to the test thresholds, in Step 1660. As mentioned above, in one example, the conveyance or portion of the conveyance may be rescanned, new TRs calculated, and the new TRs compared to the test threshold set.

TRs are again grouped based on the comparison, in Step 1662, as described above with respect to Step 1656. The group size may be smaller than that used in Step 1656, and different criteria (the criteria described above) may be applied to the groups. Appropriate group sizes are discussed above in Step 1662, as is described above with respect to Step 1656, to determine the at least potential presence of HANM, as described with respect to the methods of FIGS. 8, 10, and/or 12, for example.

It is then determined whether the contents of the object at least potentially include HANM based, at least in part, on the application of the criteria to the groups, as described above with respect to the methods of FIGS. 8, 10, and/or 12, or other methods. As above, if less sensitivity/specificity is acceptable, then grouping need not be applied. It may then be determined whether HANM is at least potentially present by comparing the number of TRs in the whole object or a portion of the object below (or above) the threshold to a predetermined number, for example.

Different test thresholds or threshold sets may be applied to different sections of the same conveyance if their contents are found to differ in the preliminary tests of Steps 1652-1658. For example, if one or more sections of the cargo conveyance is found to at least potentially comprise inorganic material, and the remainder is found to at least potentially comprise organic material (or vice-a-versa), then an inorganic based threshold may be used on the inorganic portion and an organic based threshold may be used on the organic portion. Each section may comprise at least about 10% of the cargo conveyance, for example. The section may be about 25% or about 50% of the cargo conveyance, for example.

In another embodiment, the tests described above are run by the computer 2200 or another such processor with a high sensitivity preliminary threshold set for either inorganic or organic material. The high sensitivity threshold set comprises thresholds chosen to maximize sensitivity at the expense of specificity, giving greater confidence of identifying the presence of HANM, but also allowing more false positives. In one example, a high sensitivity threshold is a threshold having a sensitivity of at least 80%, calculated without regard to specificity. In another example, the sensitivity is at least about 90%. It may be about 99%, for example. The specific sensitivity used may depend on the threat level and throughput of the port or other location conducting the test, for example. Threshold calculation based on a test piece is described in detail, above.

In one example, the preliminary test is conducted with either a high sensitivity organic or inorganic threshold set, based on the manifest, for example. In another example, a default high sensitivity threshold is either an inorganic based threshold, or an organic based threshold, regardless of the manifest. In this second example, one or the other threshold set may be selected based on the type of material usually handled by a facility, for example. The threshold set may be calculated to have sufficient sensitivity to identify the at least potential presence of HANM regardless of the background, by selection of an appropriate number of standard deviations. One of ordinary skill in the art could calculate such thresholds based on the test pieces and the desired sensitivity level, as described in more detail above. With such a threshold set, if no HANM is at least potentially identified by the tests above with the high sensitivity threshold set, then no further examination of the conveyance is required.

If HANM is at least potentially identified, further analysis is required to eliminate false positives. A false positive may be due to the effect of background material on detected radiation. In one example, the material type of the background material is determined and if the high sensitivity threshold set was based on the same material type, then the use of the high sensitivity threshold would be sufficient to identify the potential presence of HANM with a low false positive rate. If the background material type does not match the threshold material type, then, in one example, a more specific threshold set for the background material type is selected and used in the dual energy analysis of the data. A more specific threshold set may be developed by one of ordinary skill in the art in accordance with the teachings of the present application, based on the desired sensitivity at the port or other location of interest conducting the test, including the threat level and throughput of the location, for example. A specificity of at least about 80%, such as at least about 90%, at least about 99%, or at least about 99.9%, for example, may be provided. A specificity of about 99% (allowing about 1% false positives) may be provided using 2.7 standard deviations, while a specificity of about 90% (allowing about 10% false positives) may be provided using 1.7 standard deviations, for example.

In another example, to eliminate false positives after identifying potential HANM with the high sensitivity threshold set, the detected radiation is normalized for the background, as discussed above, by subtracting the average background transmission at each energy endpoint from the pixel values at each corresponding energy endpoint. The TRs are then calculated again, with the background attenuation removed. Dual energy analysis is conducted again with a high specificity threshold set of the same material type as the first threshold set. For example, if the high sensitivity threshold set is based on iron, the high specificity threshold set may also be based on iron.

The background material (the material around the suspected HANM) in the conveyance is analyzed to determine whether it is inorganic or organic material, in a similar manner as the contents of the conveyance is analyzed to determine the material content type as organic or inorganic, as above. The boundaries of the potential HANM are first identified, as discussed above with respect to FIG. 6b. The TRs of the pixels outside of the boundaries of the potential HANM may then be compared to a preliminary test threshold based on a material having an atomic number between organic and common inorganic materials, such as aluminum (Z=13), for example. Pixels are marked and marked pixels are grouped, as discussed above with respect to FIGS. 8, 10, 12, and 14b. The groups are compared to criteria. Based on the comparison, it is determined whether the background is likely to be organic or inorganic material, as described above with respect to FIG. 14b, Step 1658.

The calculated TRs may then be normalized with respect to the background by dividing the detected radiation by the average radiation of the background, for each portion or pixel at each detected energy, as described above with respect to FIG. 6b, for example.

Figure 14C:
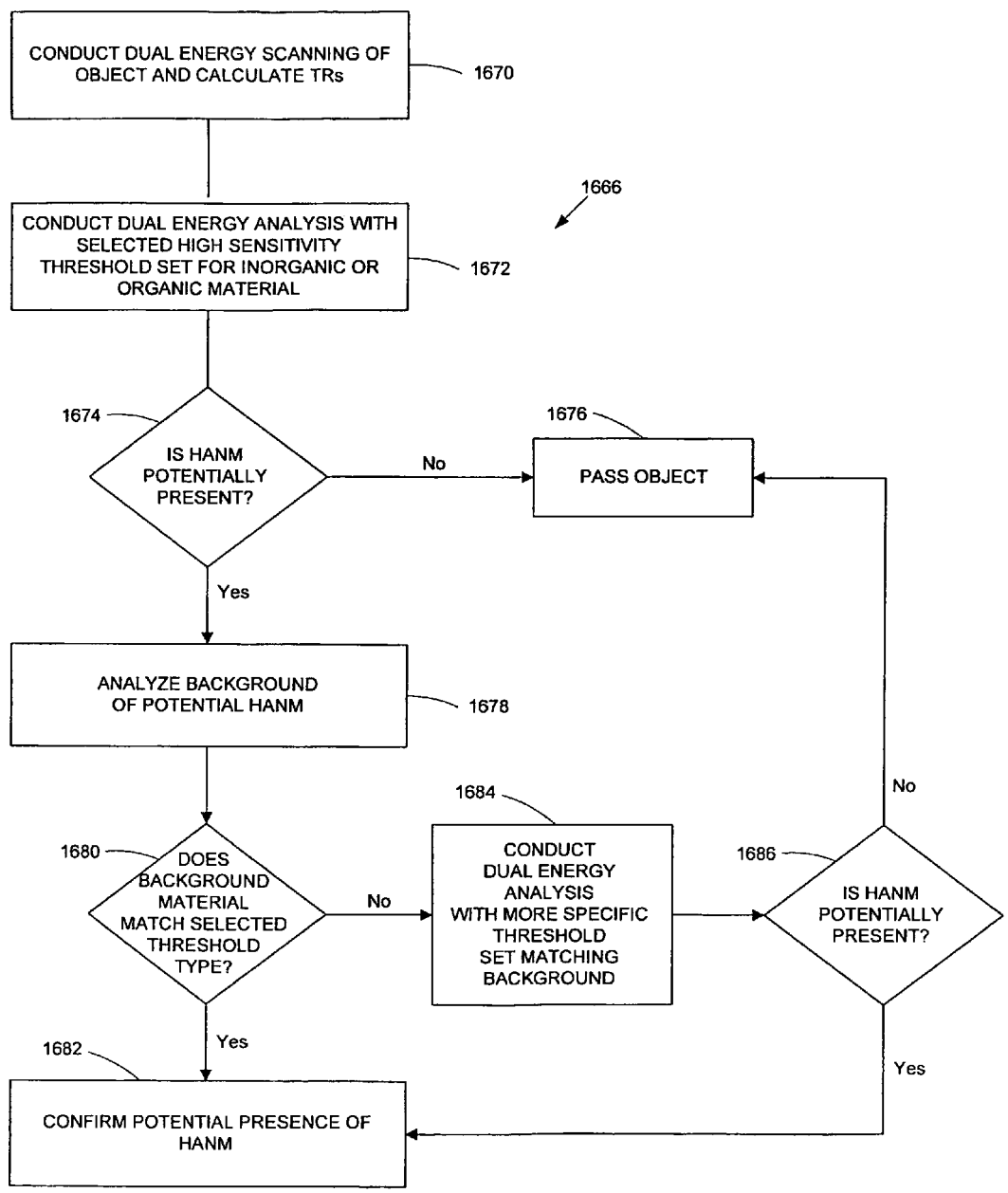
FIG. 14c is an example of a method for examining contents of an object, in accordance with another embodiment of the invention.

FIG. 14c is an example of a method 1666 for examining contents of conveyance, in accordance with this embodiment. Dual energy scanning is conducted and TRs calculated, as described herein, in Step 1670. A dual energy analysis of the calculated TRs is conducted with a selected high sensitivity threshold set for either inorganic or organic material, in Step 1672, wherein the calculated TRs are compared to the appropriate threshold in the threshold set, based on the transmission at one of the energies.

As discussed above, the high sensitivity threshold set used with a particular cargo conveyance may be selected based on the manifest. It may also be based on the type of materials usually handled by a facility. Or a default material type may be used for all cargo conveyances. TRs are grouped based on the comparisons, and preliminary test criteria are applied to functions of the groups, as in Steps 1654 and 1656 of FIG. 14b, and FIGS. 8, 10, and/or 12. The at least potential presence of HANM is then determined based on the application of the test criteria to functions of the groups, in Step 1674, as described above with respect to Step 1664 of FIG. 14b, and FIGS. 8, 10, and/or 12. The groups Step 1656 and in Step 1664 need not be the same.

If no potential HANM is identified based on the high sensitivity threshold, then the conveyance is passed and can continue in the stream of commerce, in Step 1676.

If HANM is found to be potentially present, then the background of the potential HANM is analyzed in Step 1678 to determine whether the background matches the background type of the threshold set used in Step 1672. As described above, the dual energy analysis may be applied to the area around the potential HANM, with a preliminary threshold between organic and inorganic materials, as described above.

If it is determined that the background material matches the material type of the threshold set, in Step 1680, then the potential presence of HANM is confirmed, in Step 1682, and the conveyance is removed from the steam of commerce and handled appropriately, as described herein.

If the background material does not match the material type of the threshold set, then the determination that HANM is potentially present may be a false positive. Dual energy analysis is therefore conducted with a more specific threshold set that matches the type of background material, in Step 1684. The TRs are compared to the appropriate threshold, the marked TRs are grouped, and criteria applied to the groups, as discussed above.

If HANM is not found to be potentially present, in Step 1686, then the conveyance is passed, in Step 1676. If HANM is again found to be present, in Step 1686, then the potential presence of HANM is confirmed, in Step 1682, and the conveyance is appropriately processed.

As above, if less specificity is needed, then grouping need not be applied. It may then be determined whether inorganic or organic material is present, and/or HANM is at least potentially present, by comparing the number of TRs in the object or a portion of the object below (or above) the threshold to a predetermined number, for example.

Figure 14D:
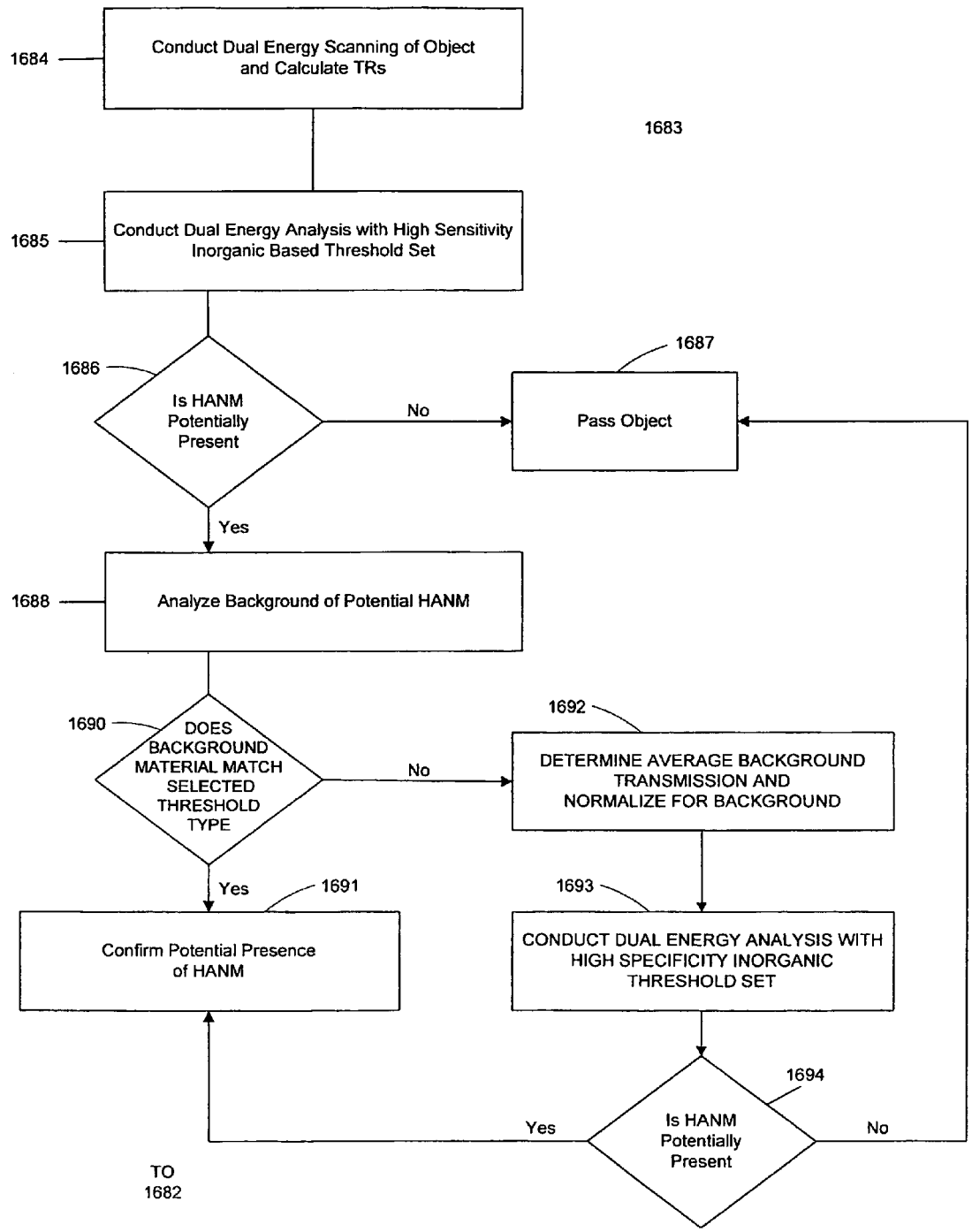
FIG. 14d is another example of a method for examining contents of an object in accordance with the embodiment of FIG. 14c.

FIG. 14*d* is another example of a process 1683 in accordance with this embodiment. Steps 1684-1690 of FIG. 14*d* are the same as Steps 1670-1680 of 14*c*. If it is determined that the background material type does not match the material type of the high sensitivity threshold set, in Step 1690 in FIG. 14*d*, the average background transmission through the background region is determined for each energy endpoint and the transmissions through the potential HANM at each energy endpoint are normalized based on the average background transmission, in Step 1689, as described in FIG. 6*b*. The dual energy analysis is conducted again in Step 1690 with a high specificity threshold set. The TRs of the potential HANM are calculated again, the TRs are compared to the thresholds in the high specificity threshold set, the appropriate TRs are grouped, and criteria are applied to the groups, as described in FIGS. 6*a*, 8, 10, and/or 12.

The high specificity threshold set used in Step 1690 may be based on the same material type as the high sensitivity threshold set used in Step 1685, such as iron, for example. After background normalization, SNM and other suspect HANM can be readily identified with an iron or other such inorganic threshold, regardless of the background effects of the material since the background has been removed. If HANM is at least potentially identified again, then SNM may be present and the cargo conveyance is subject to further analysis. If HANM is not potentially identified, the cargo conveyance is passed.

As above, if less sensitivity is needed, then grouping need not be applied. It may then be determined whether inorganic or organic material is present, and/or HANM is at least potentially present, by comparing the number of TRs below (or above) the threshold to a predetermined number, for example.

Scanning Systems

Figure 15:
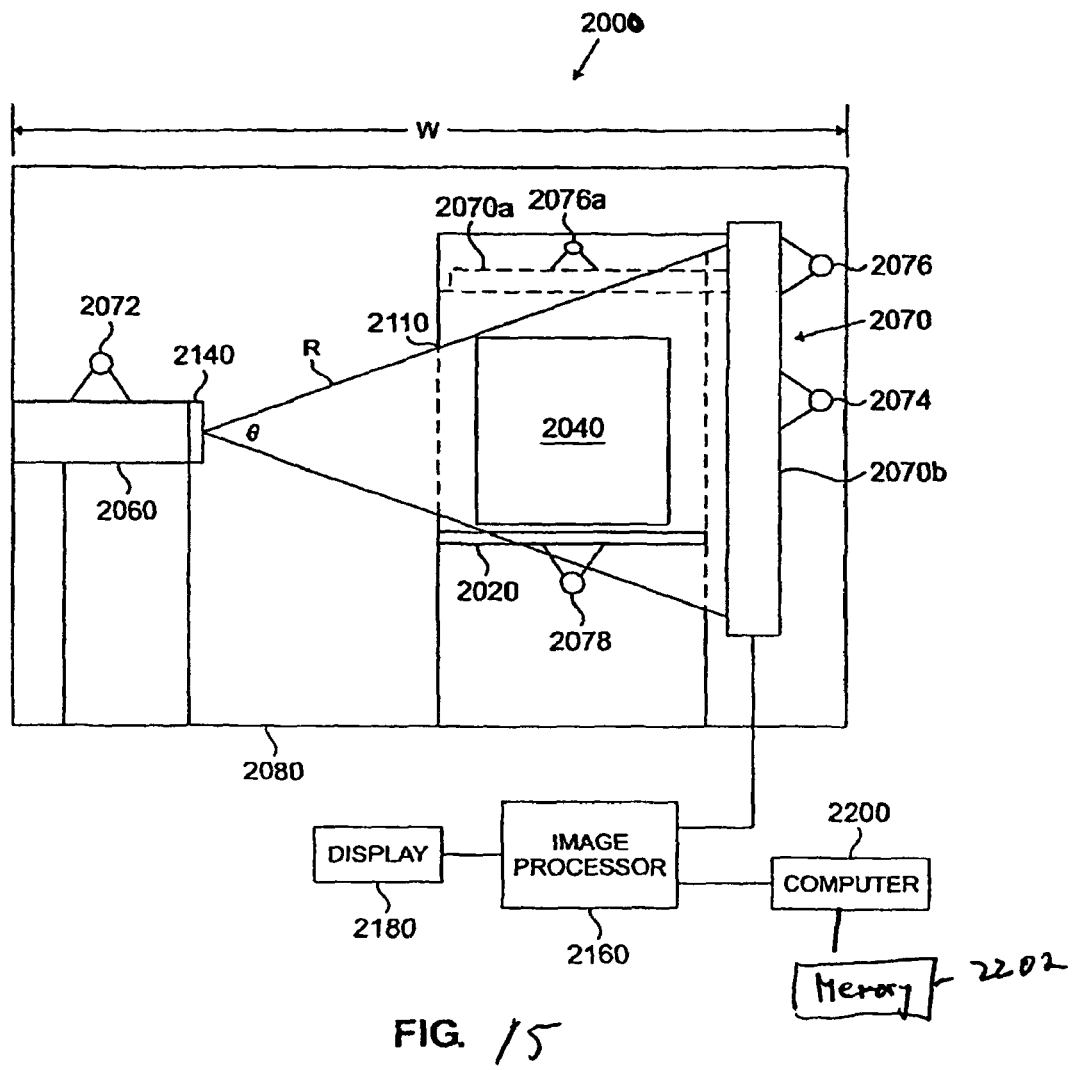
FIG. 15 is a front view of a cargo scanning system programmed to implement embodiments of the invention.

FIG. 15 is a front view of an example of cargo scanning system 2000 programmed to implement embodiments of the invention. A conveyor system 2020 supports and conveys a cargo conveyance 2040 through the scanning system 100, between an X-ray source 2060 and a detector 2070. The conveyor system 2020 may be a mechanically driven conveyor belt, a track or mechanically driven rollers, for example. The X-ray source 2060 directs a radiation beam R of Bremsstrahlung X-ray radiation towards the cargo conveyance 2040. Shielding walls 2080 surround the source 2060 and the detector 2070. The conveyor system 2020 extends through openings in the shielding walls 2080 to allow for the entry and exit of the cargo conveyance 2040.

The cargo conveyance 2040 is conveyed by the conveyor system 2020 through a shielded tunnel 2100. The tunnel 2100 has a first window 2110 and a second window 2120 to allow for the passage of the X-ray radiation beam R from the X-ray source 2060 to the cargo conveyance 2040 and from the cargo conveyance 2040 to the detector array 2070. If the radiation beam R intercepts the conveyor system 2040 and the conveyor system 2020 is a belt or track, a material that causes low attenuation of radiation may be used for the belt or track. If the conveyor system 2020 comprises rollers, a gap may be provided among the plurality of rollers, where necessary. A window may also be provided in the structure supporting the conveyor system 2020, if necessary. Collimators (not shown) may be provided between the cargo conveyance 2040 and the detector 2070 to block scattered radiation from reaching the detector. The conveyor system 2020 may be reversed to examine a portion of the cargo conveyance 2040 or the entire cargo conveyance again. As discussed further below, the cargo conveyance 2040 may be irradiated with multiple energies by rapidly cycling the source 2060 between two energy endpoints as the cargo conveyance 104 is being conveyed through the scanning unit 2000 or by providing two adjacent sources, for example.

A collimator 2140 extends from the end of the X-ray source 2060. The collimator 2140 includes a slot (not shown) shaped to collimate the X-ray beam emitted by the X-ray source 2060 into a desired shape, such as into a fan beam or a cone beam. The slot may have a vertical arc ranging from less than 1 degree to about 50 degrees to define a vertical fan beam having an arc θ and ranging from about 5 degrees to about 45 degrees to define a cone beam, for example. The slot may have other shapes, as well.

The detector 2070 is electrically coupled to an image processor 2160, which is coupled to a display 2180. The image processor 2160 comprises analog-to-digital conversion and digital processing components, as is known in the art. A processor, such as a computer 2200, is electrically coupled to and controls the operation of one or more of the X-ray source 2060, the detector array 2040, the conveyor system 2020, the image processor 2160, and the display 2180. Connections between the processor 122 and all the components are not shown, to simplify the Figure. The processor 2200 may be programmed to implement any or all of the tests described above. The processor 2200 may provide some or all of the processing functions of the image processor 2160. While one processor 2200 is shown, additional processors or computers may be provided, as well. The image processor 2160, the computer 2200 and the display 2180 may be arranged and connected differently. The image processor 2160 may be part of the computer, for example. The computer may be programmed in software and/or hardware to conduct any or all of the tests described above. In one example, the programs may be implemented through an Application Specific Integrated Circuit (ASIC) for example.

The detector 2070 may be a detector array. The configuration of the detector 2070 may depend on the shape of the collimated radiation beam R. For example, if the radiation beam R is collimated into a fan beam, a one-dimensional detector array 2040 may be provided, comprising a single row of detector elements. If the collimated radiation beam is a cone beam, such as an asymmetric pyramidal cone beam, the detector array may be a two dimensional detector array 2040 comprising two or more adjacent rows of detector elements. The detector array 2040 may comprise a plurality of modules of detectors, each comprising one or more rows of detector elements supported in a housing, as is known in the art. The detector or detector array may be straight or L-shaped. If an L-shaped detector is used in FIG. 15, the source 2060 may be positioned at a lower vertical position, the radiation beam R would intercept more of the horizontal arm 2070*a* and the vertical portion 2070*b* of the detector 2070 may be shorter.

The detector 2070 may be a photon detector, such as a photodiode detector array comprising inorganic scintillators, as is known in the art. Cadmium tungstate ($CdWO_4$) scintillators may be used, for example. Amorphous silicon (aSi) detectors, such as PaxScan™ detectors available from Varian Medical Systems, Inc., Palo Alto, Calif., may also be used.

Neutron detectors 2072, 2074, 2076, and 2078 are preferably positioned at multiple locations around the cargo container to detect the neutrons, which are emitted isotropically in all directions. The neutron detector 2072 may be supported by the source, for example. The neutron detector 2074 may be supported by the detector 2070. The neutron detector 2076 may be supported by the upper portion of the detector 2070 or by a vertical arm of an L-shaped detector (see 2076*a*). The neutron detector 2078 may be supported by the conveyor system 2020 or some other part of the scanning system, below the cargo conveyance 2040.

The neutron detectors 2072-2078 may be cylindrical proportional counters filled with $^3$He. They may have useful lengths of approximately 15-25 cm for use with cargo conveyances 2040, for example. In one example, the counters are covered with cadmium (Cd) and polyethylene layers. The layer of cadmium is used to absorb thermal neutrons which are "slow" neutrons. Fast neutrons are thermalized in the polyethylene layer before being detected in the $^3$He detectors. Only the delayed neutrons are therefore detected in the $^3$He detectors. Suitable neutron detectors are commercially available from Canberra Industries, Meriden, Conn., for example.

FIG. 17 is a top view of a portion of an example of a cargo scanning system 2000*a*, showing two, adjacent radiation sources 2060*a*, 2060*b*, each to generate radiation having a different energy endpoint. Elements common to the system 2000 of FIG. 16 are commonly numbered. The conveyor system 2020 supports and conveys a cargo conveyance 2040 through the scanning system 2000*a*, between the first X-ray source 2060*a* and a first detector 2070*a*, and between the second X-ray source 2060*b* and a second detector 2070*b*. The X-ray sources 2060*a* and 2060*b* direct radiation beams R1, R2 towards the cargo conveyance 2040. The X-ray source 2060*a* may generate a first radiation beam R1 with a first X-ray energy endpoint of 5 MeV, for example, and the X-ray source 2060*b* may generate a second radiation beam R2 with a second energy endpoint of 9 MeV, for example, or vice-versa. The X-ray sources 2060*a* and 2060*b* are positioned at the same angle with respect to the cargo conveyance 2040 and on the same horizontal plane. They may be immediately adjacent to or may be situated apart from each other. They may also be positioned one above the other. It is believed that in a system with two sources, a 40-foot container may be examined in about 30 to 60 seconds.

To examine cargo conveyances 2040 having a width greater than about 5 feet (1.5 meters), the X-ray sources 2060*a*, 2060*b* preferably generate radiation having energy endpoints greater than about 1 MeV. 5 MeV and 9 MeV may be used, for example, as discussed above. Other examples of energy endpoints for cargo conveyances having a width greater than about 5 feet (1.5 meters) include 1 MeV and 9 MeV, and 5 MeV and 15 MeV, for example. In order to conduct the neutron test, one of the energy endpoints needs to be at least 5.8 MeV. The X-ray source may be a linear accelerator, such as a Linatron® Linear Accelerator ("Linatron®"), having an accelerating potential at an appropriate level or levels, available from Varian Medical Systems, Inc., Palo Alto, Calif. ("Varian"), for example. In the Varian Linatron®, 360 pulses are output per second. The Varian Linatron® has an opening angle of about 20-30 degrees, for example. Other X-ray sources may be used as well, such as electrostatic accelerators, microtrons and betatrons, for example. The source or sources may also include carbon-12 (C-12), cobalt-60 (Co-60), plutonium-beryllium (Pu—Be), and/or americium-beryllium (Am—Be) based sources. In examining objects having a width less than about 5 feet (1.5 meters), X-ray tubes emitting energy in the keV range may also be used. One energy below 1 MeV and one above 1 MeV may be used for such smaller objects. For example, 600 keV and 5 MeV may be used. Both energies may also be below 1 MeV. For example, 120 keV and 200 keV may be used, as long as the radiation will penetrate through the object being examined.

A single X-ray beam having a single energy endpoint may also be used, with a single energy sensitive detector array to separately detect high and low portions of the energy spectrum, as described in U.S. Pat. Nos. 5,682,411 and 6,438,201 B1, for example, which are incorporated by reference, herein. As described in these patents, different portions of the detector array, such as alternate lines, may be more sensitive to radiation of one or the other energy.

A single radiation source that switches between energy endpoints may also be used. The radiation source may be an interlaced multi-energy radiation source capable of generating radiation beams at two or more energies in the megavolt-age range, such as the Varian Linatron® M™ series X-ray sources. An example of the Linatron® M™ radiation source is described in U.S. patent application Ser. No. 12/228,350, which was filed on Aug. 12, 2008 and is incorporated by reference herein. Another example of an interlaced multi-energy source is the Varian Linatron® K-9, which is described in U.S. patent application Ser. No. 12/313,752, which was filed on Nov. 24, 2008 and is incorporated by reference herein.

Other radiation sources that may be configured to switch between different peak energies are described in the '188 patent, which is incorporated by reference herein.

Additional X-ray scanning and/or analysis techniques may be used in conjunction with the tests described herein. For example, in the '188 patent and in U.S. Pat. No. 7,423,273, which are assigned to the assignee of the present invention and are incorporated by reference herein, the detection of delayed neutrons is used to determine whether nuclear material is actually present, after at least potentially determining that HANM is present.

While the scanning system 2000 described above moves the cargo conveyance through the system on a conveyor belt, track, or mechanically driven rollers, for example, the cargo conveyance may also be part of or supported by a truck. U.S. Pat. Nos. 7,397,891, and 6,937,692, which are assigned to the assignee of the present invention and are incorporated by reference herein, describe a mobile system for real-time inspection of cargo conveyances carried by trucks and tractor trailers.

While the invention is particularly suited for scanning cargo conveyances for contraband, the invention may be readily adapted to scan other objects, such as luggage and carry-on bags in airports and seaports. In addition, while an X-ray source or sources are described in the examples above, the source or sources may provide other types of radiation, such as a time delayed neutron beam or gamma rays, for example.

In the examples above, the transmission of the higher energy radiation (9 MeV, for example) through the cargo conveyance is divided by the transmission of the lower energy radiation (5 MeV, for example) through the cargo conveyance to yield the TR and the test criterion for a potential HANM is that the TR is less than the threshold. However, as mentioned above, the transmission at the lower energy radiation may be divided by the transmission at the higher energy radiation, in which case a TR above the threshold would be considered to be a potential HANM, in all the examples, above. In addition, TRs may be calculated based on radiation attenuation instead of radiation transmission at the two energy endpoints.

One of ordinary skill in the art will recognize that other changes may be made to the embodiments described herein without departing from the spirit and scope of the invention, which is defined by the claims, below.

What is claimed is:

1. A method of examining contents of an object, the method comprising:
    scanning the object with at least one radiation energy;
    detecting the radiation after interaction with the object;
    determining whether the contents of the object comprise organic or inorganic material based, at least in part, on the detected radiation and at least one preliminary test criterion adapted to differentiate between inorganic material and organic material;
    selecting at least one organic based test criterion or at least one inorganic based test criterion based, at least in part, on the determination; and
    determining whether the object at least potentially contains high atomic number material having an atomic number greater than a predetermined atomic number based, at least in part, on the detected radiation and the at least one selected test criterion.

2. The method of claim 1, wherein the at least one preliminary test criterion comprises at least one high sensitivity test criterion representative of organic material, or the at least one preliminary test criterion is based, at least in part, on a material having an atomic number less than the atomic number of iron and greater than the atomic number of oxygen.

3. The method of claim 1, further comprising:
    detecting radiation at two different energies after interaction with a portion of the object;
    calculating a first function of the detected radiation at the two different radiation energies, for the portion;
    comparing the first function to the at least one preliminary test criterion; and
    determining whether the contents of the object comprise organic or inorganic material based, at least in part, on the first function and the comparison.

4. The method of claim 3, further comprising:
    calculating a plurality of first functions for a respective plurality of portions;
    comparing respective first functions to the at least one preliminary test criterion;
    grouping the first functions into at least one group;
    calculating at least one second function for each of the at least one groups based, at least in part, on the first functions in the at least one group meeting the at least one preliminary test criterion; and
    determining whether the object at least potentially contains inorganic material or organic material based, at least in part, on the at least one second function of the at least one group.

5. The method of claim 4, wherein determining whether the object at least potentially contains high atomic number material having an atomic number greater than a predetermined atomic number comprises:
    calculating at least one third function of the detected radiation at the two different radiation energies for at least a portion of the object;
    comparing the at least one third function to the at least one selected test criterion; and
    determining whether the object at least potentially contains high atomic number material based, at least in part, on the comparison.

6. The method of claim 5, wherein the calculated at least one third function is the same as the calculated at least one first function, the method comprising:
    comparing the calculated at least one first function to the selected test criterion.

7. The method of claim 5, wherein determining whether the object at least potentially contains high atomic number material further comprises:
    calculating a plurality of third functions;
    grouping the plurality of third functions into at least one second group;
    calculating at least one fourth function based, at least in part, on the third functions in the at least one group meeting the at least one selected test criterion; and
    determining whether the object at least potentially contains high atomic number material based, at least in part, on the at least one fourth function.

8. The method of claim 7, wherein the at least one first group of first functions and the at least one second group of third functions are the same size.

9. The method of claim 7, wherein:
    selecting at least one organic based test criterion comprises selecting an organic based test criterion set comprising a plurality of first test criteria, and
    selecting at least one inorganic based test criterion comprises selecting an inorganic based test criterion set comprising a plurality of second test criteria.

10. The method of claim 1, comprising:
    detecting radiation at two different energies after interaction with a portion of the object;
    calculating at least one first function of the detected radiation at the two different energies;
    comparing the at least one first function to the at least one selected test criterion; and
    determining whether the object at least potentially contains high atomic number material based, at least in part, on the comparison.

11. The method of claim 10, wherein determining whether the object at least potentially contains high atomic number material further comprises:
    calculating a plurality of first functions;
    grouping first functions into at least one group;
    calculating at least one second function based, at least in part, on the first functions in at least one respective group meeting the at least one selected test criterion; and
    determining whether the object at least potentially contains high atomic number material based, at least in part, on the at least one second function;

the method further comprising:

calculating a plurality of first functions at the two different radiation energies for a respective plurality of portions; and comparing the first functions to the selected test criterion comprises:

for each first function, selecting one of the plurality of test criteria based, at least in part, on the radiation detected at at least one of the radiation energies; and comparing each first function to the respective selected test criterion.

12. The method of claim 1, comprising:

determining whether the object at least potentially contains high atomic number material having an atomic number greater than the predetermined atomic number based, at least in part, on the detected radiation and at least one high sensitivity test criterion of a first type based, at least in part, on a first predetermined atomic number representative of inorganic material, or at least one high sensitivity test criterion of a second type based, at least in part, on a second predetermined atomic number representative of organic material.

13. The method of claim 1, further comprising:

classifying a type of background material proximate the at least potential high atomic number material as either inorganic material or organic material based, at least in part, on the detected radiation; and if the type of test criterion matches the type of background material, confirming that the object at least potentially contains high atomic number material.

14. The method of claim 13, further comprising:

if the type of test criterion and the type of the background material do not match, the processor is further configured to:

normalize the radiation detected through the at least potential high atomic number material for the presence of the background material;

select at least one second test criterion of the same type as the at least one first test criterion, the at least one second test criterion having greater specificity to high atomic number material than the at least one first test criterion; and confirm that the object at least potentially contains high atomic number material based, at least in part, on the normalized detected radiation and the at least one second test criterion.

15. A method of examining contents of an object comprising:

scanning an object with at least one radiation beam;

detecting the radiation after interaction with the object;

determining whether the object at least potentially contains high atomic number material having an atomic number greater than the predetermined atomic number based, at least in part, on the detected radiation and at least one high sensitivity test criterion of a first type based, at least in part, on a first predetermined atomic number representative of inorganic material, or at least one high sensitivity test criterion of a second type based, at least in part, on a second predetermined atomic number representative of organic material;

classifying a type of background material proximate the at least potential high atomic number material as either inorganic material or organic material based, at least in part, on the detected radiation; and if the type of test criterion matches the type of background material, confirming that the object at least potentially comprises high atomic number material.

16. The method of claim 15, wherein, if the type of test criterion and the type of the background material do not match, the method further comprises:

normalizing the radiation detected through the at least potential high atomic number material for the presence of the background material;

selecting at least one second test criterion of the same type as the at least one first test criterion, the at least one second test criterion having greater specificity to high atomic number material than the at least one first test criterion; and confirming that the object at least potentially contains high atomic number material based, at least in part, on the normalized detected radiation and the at least one second test criterion.

17. The method of claim 15, wherein, if the type of test criterion and the type of background material do not match, the method further comprises:

selecting at least one second, high sensitivity test criterion of a type matching the type of the background material; and confirming that the object at least potentially comprises high atomic number material based, at least in part, on the detected radiation and the second test criterion.

18. The method of claim 15, comprising classifying the type of background material based, at least in part, on the detected radiation and at least one preliminary test criterion adapted to differentiate between inorganic material and organic material.

19. The method of claim 18, wherein the at least one preliminary test criterion is based, at least in part, on a material having an atomic number less than the atomic number of iron and greater than the atomic number of oxygen, or the preliminary test criterion is a high sensitivity preliminary test criterion based, at least in part, on a material representative of organic material.

20. The method of claim 15, wherein the at least one high sensitivity threshold of the first type and the at least one high sensitivity threshold of the second type each have a sensitivity of at least 80%.

21. A system for examining contents of an object, the system comprising:

at least one radiation source to scan an object with at least one radiation energy;

at least one detector to detect radiation after interaction with the object, at the at least one radiation energy; and a processor configured to:

determine whether the contents of the object comprise organic or inorganic material;

select at least one test criterion based, at least in part, on whether the contents of the object comprises organic or inorganic material; and determine whether the contents of the object at least potentially contains high atomic number material having an atomic number greater than a predetermined atomic number based, at least in part, on the detected radiation and the at least one selected test criterion.

22. The system of claim 19, wherein the processor is configured to:

determine whether the contents of the object comprise organic or inorganic material based, at least in part, on the detected radiation and at least one preliminary test criterion different than the at least one selected test criterion, the at least one preliminary test criterion being adapted to distinguish between inorganic and organic material.

23. The system of claim 22, wherein the processor is configured to:
- determine whether the contents of the object comprise organic or inorganic material by:
- calculating at least one first function of the detected radiation at the two different radiation energies, for at least one respective portion;
- compare each of the at least one first functions to the at least one preliminary test criterion; and
- determine whether the contents of the object comprise organic or inorganic material based, at least in part, on the first function and the comparison.

24. The system of claim 23, wherein the at least one preliminary test criterion comprises a preliminary test criterion set comprising a plurality of preliminary test criteria, and the processor is configured to determine whether the object comprises organic or inorganic material by:
- calculating a plurality of first functions for a respective plurality of portions;
- comparing respective first functions to the at least one preliminary test criterion;
- grouping the first functions into at least one group;
- calculating at least one second function for each of the at least one groups based, at least in part, on the first functions in the at least one group meeting the at least one preliminary test criterion; and
- determining whether the contents of the object contains inorganic material or organic material based, at least in part, on the second function of the at least one group.

25. The system of claim 22, wherein the processor is configured to:
- determine whether the object at least potentially contains high atomic number material having an atomic number greater than the predetermined atomic number based, at least in part, on the detected radiation and at least one high sensitivity test criterion of a first type based, at least in part, on a first predetermined atomic number representative of inorganic material, or at least one high sensitivity test criterion of a second type based, at least in part, on a second predetermined atomic number representative of organic material;
- classify a type of background material proximate the at least potential high atomic number material as either inorganic material or organic material based, at least in part, on the detected radiation; and
- if the type of test criterion matches the type of background material, confirm that the object at least potentially contains high atomic number material.

26. The system of claim 25, wherein, if the type of test criterion and the type of the background material do not match, the processor is further configured to:
- normalize the radiation detected through the at least potential high atomic number material for the presence of the background material;
- select at least one second test criterion of the same type as the at least one first test criterion, the at least one second test criterion having greater specificity to high atomic number material than the at least one first test criterion; and
- confirm that the object at least potentially contains high atomic number material based, at least in part, on the normalized detected radiation and the at least one second test criterion.

27. The system of claim 25, wherein, if the type of test criterion does not match the type of background material, the processor is further configured to:
- select at least one second, high sensitivity test criterion of a type matching the type of the background material; and
- confirm that the object at least potentially contains high atomic number material based, at least in part, on the detected radiation and the second test criterion.

28. A system for examining contents of an object, the system comprising:
- at least one radiation source to scan an object with at least one radiation beam;
- at least one detector to detect radiation after interaction with the object;
- a processor configured to:
- determine whether the object at least potentially contains high atomic number material having an atomic number greater than the predetermined atomic number based, at least in part, on the detected radiation and at least one high sensitivity test criterion of a first type based, at least in part, on a first predetermined atomic number representative of inorganic material, or at least one high sensitivity test criterion of a second type based, at least in part, on a second predetermined atomic number representative of organic material;
- classify a type of background material proximate the at least potential high atomic number material as either inorganic material or organic material based, at least in part, on the detected radiation; and
- if the type of test criterion matches the type of background material, confirm that the object at least potentially comprises high atomic number material.

29. The system of claim 28, wherein, if the type of test criterion and the type of the background material do not match, the processor is further configured to:
- normalize the radiation detected through the at least potential high atomic number material for the presence of the background material;
- select at least one second test criterion of the same type as the at least one first test criterion, the at least one second test criterion having greater specificity to high atomic number material than the at least one first test criterion; and
- confirm that the object at least potentially contains high atomic number material based, at least in part, on the normalized detected radiation and the at least one second test criterion.

30. The system of claim 28, wherein, if the type of test criterion and the type of background material do not match, the processor is configured to:
- select at least one second, high sensitivity test criterion of a type matching the type of the background material; and
- confirm that the object at least potentially comprises high atomic number material based, at least in part, on the detected radiation and the second test criterion.

31. The system of claim 28, wherein the processor is configured to:
- classify the type of background material based, at least in part, on the detected radiation and at least one preliminary test criterion adapted to differentiate between inorganic material and organic material.

32. The system of claim 28, wherein the at least one preliminary test criterion is based, at least in part, on a material having an atomic number less than the atomic number of iron and greater than the atomic number of oxygen, or the preliminary test criterion is a high sensitivity preliminary test criterion based, at least in part, on a material representative of organic material.

33. The system of claim 28, wherein the at least one high sensitivity threshold of the first type and the at least one high sensitivity threshold of the second type each have a sensitivity of at least 80%.

* * * * *